US011786473B2

(12) United States Patent
Nielsen et al.

(10) Patent No.: US 11,786,473 B2
(45) Date of Patent: Oct. 17, 2023

(54) NICOTINE TABLET

(71) Applicant: Fertin Pharma A/S, Vejle (DK)

(72) Inventors: Kent Albin Nielsen, Brande (DK); Rikke Pranger-Rasmussen, Vejle (DK); Dorthe Schackinger Boesen, Vejle (DK); Heidi Ziegler Bruun, Vejle Øst (DK); Bruno Provstgaard Nielsen, Vejle Øst (DK)

(73) Assignee: Fertin Pharma A/S, Vejle (DK)

( * ) Notice: Subject to any disclaimer, the term of this patent is extended or adjusted under 35 U.S.C. 154(b) by 0 days.

(21) Appl. No.: 17/644,182

(22) Filed: Dec. 14, 2021

(65) Prior Publication Data

US 2023/0181478 A1 Jun. 15, 2023

(51) Int. Cl.
*A61K 9/20* (2006.01)
*A61K 31/4439* (2006.01)

(52) U.S. Cl.
CPC .......... *A61K 9/2086* (2013.01); *A61K 9/2009* (2013.01); *A61K 9/2013* (2013.01); *A61K 9/2018* (2013.01); *A61K 31/4439* (2013.01)

(58) Field of Classification Search
None
See application file for complete search history.

(56) References Cited

U.S. PATENT DOCUMENTS

| 2014/0328973 | A1* | 11/2014 | Nielsen | A23G 4/06 426/5 |
| 2015/0157620 | A1* | 6/2015 | Berthoumieu | B05D 1/02 514/343 |
| 2019/0174812 | A1* | 6/2019 | Nielsen | A61K 9/2009 |
| 2021/0290530 | A1 | 9/2021 | Wittorff | |
| 2021/0378948 | A1 | 12/2021 | Gerardi et al. | |

FOREIGN PATENT DOCUMENTS

| CA | 2737307 A1 | 4/2010 |
| WO | WO2022063372 A1 | 3/2022 |
| WO | WO2022224197 A1 | 10/2022 |

OTHER PUBLICATIONS

International Search Report dated Apr. 13, 2023 in International Application No. PCT/EP2022/085827, 6 pages.

* cited by examiner

*Primary Examiner* — Susan T Tran
(74) *Attorney, Agent, or Firm* — Lee & Hayes, P.C.

(57) ABSTRACT

A water-dissolvable nicotine tablet is disclosed, the nicotine tablet comprising at least a first compressed module and a second compressed module, wherein the first compressed module is an FDT-module and comprises nicotine, alkaline pH regulating agent, and disintegrant, and, wherein the second compressed module is a lozenge-module and comprises acidic pH regulating agent. Also, a method of manufacturing a nicotine tablet is disclosed.

18 Claims, No Drawings

NICOTINE TABLET

FIELD OF THE INVENTION

The invention relates to a nicotine tablet and a method of making a such nicotine tablet.

BACKGROUND

Oral tobacco compositions are known to cause an undesirable sensation in the throat of the users.

This is often referred to as a burning sensation.

The present invention addressed this challenge by providing a nicotine delivery vehicle being particularly optimized towards an improved user expectation and experience.

SUMMARY

The invention relates to a water-dissolvable nicotine tablet comprising at least a first compressed module and a second compressed module, wherein the first compressed module is an FDT-module and comprises
  nicotine,
  alkaline pH regulating agent, and
  disintegrant, and,
wherein the second compressed module is a lozenge-module and comprises
  acidic pH regulating agent.

In the present context a module is defined as a plurality of a compressed particles. An implementation of such a tablet would be a tablet consisting of two modules, a first and a second module, and where each module is a layer of the tablet. In other words, such an example would be a two-layered tablet. Another implementation of such a tablet would be a tablet consisting of two modules, a first and a second module, and where the second module is a tablet core and the first module is a compressed coating surrounding the first module i.e. tablet core. Other configurations of modules may be applied within the scope of the invention. Also, other numbers of modules may be applied within the scope of the invention.

It should be noted that the understanding of a module in the present context is a module enabling and facilitating the intended effect, i.e. an effective delivery or administration of nicotine and at the same time providing the intended masking of undesirable taste and reducing the undesirable burning sensation. This imposes some structural restrictions on the modules in the sense that modules must be large enough to be able to not only deliver the nicotine but also the desired compounds used to mask taste and reduce burning. Furthermore, the modules should facilitate release of the components at the right time.

A module in the present context thus, in an advantageous embodiment, encompasses a population of compressed particles weighing at least 10% by weight of the tablet. In other words, a module is not intended to refer to individual particles as conventionally understood from the art of tableting.

The first compressed module is designed and provided as a module which in itself is characterized by being an FDT-module, i.e. a module having the characteristics of a so-called fast disintegrating tablet. Fast disintegrating tablets, also sometimes referred to as orally disintegrating tablets (ODT), generally exhibits rapid oral disintegration with no need for chewing or drinking liquids to ingest these products.

FDT-modules of the invention exhibits fast disintegration, typically below 60 seconds from placing it in the mouth, or even faster such as 30 seconds from placing it in the mouth.

Thus, the FDT-module may also be referred to as a fast disintegrating module or a fast disintegrating tablet module.

The disintegrant contributes to the fast disintegration of the FDT-module, when the FDT-module comes into contact with saliva. Disintegrants may often be considered as measure promoting the break-up of the module into smaller fragments upon administration to facilitate nicotine release and eventual absorption.

The presence of an alkaline pH regulating agent may advantageously facilitate effective uptake of nicotine due to the high pH value obtained. An alkaline pH regulating agent is a substance, which upon dissolution in water having a pH of 7.0 increases the pH to more than 7.5 measured at 25 degrees Celsius and atmospheric pressure.

The alkaline pH regulating agent may facilitate a desirable high fraction of the unprotonated nicotine specie, i.e. nicotine free base, being present, which is available for absorption over the mucous membrane in the oral cavity. Also, the presence of alkaline pH regulating agent may facilitate a desirable high pH within the oral cavity, whereby undesirable protonation of released nicotine free base is diminished during the fast release and absorption period, i.e. within the first period of use, thereby ensuring an effective absorption of nicotine.

Thus, the presence of disintegrant and alkaline pH regulating agent in the FDT-module ensures that nicotine is released fast and being made available for transport through the mucosa and into the blood stream.

Obtaining a fast release rate of nicotine and an effective uptake/absorption may be desirable as this ensures a fast effect for the user, i.e. craving relief. Furthermore, the combination of having an effective release and an effective absorption advantageously enables a relative high exploitation of the nicotine dose within the FDT-module.

Having a relative high exploitation of the nicotine dose within the tablet may further provide a reduction of necessary nicotine dose of the tablet, without compromising the resulting effect. A lower nicotine dose may in turn result in a reduction in production cost, as nicotine may be relatively expensive, but may also assist users who want to lower their intake of nicotine. Furthermore, side-effects, such a nicotine burning, may be reduced due to the lower dose of nicotine.

In terms of the second compressed module being a lozenge-module, a lozenge is a well-known term in relation to medicated tablets intended to be dissolved or disintegrated over minutes when placed in the mouth, typically to release an active ingredient. Lozenges with different active ingredients are known, e.g. nicotine lozenges.

The lozenge-module comprises an acidic pH regulating agent.

An acidic pH regulating agent in accordance with the present invention is a substance, which upon dissolution in water having a pH of 7.0 induces a pH of less than 7.5 measured at 25 degrees Celsius and atmospheric pressure.

By providing a nicotine tablet, facilitating onset of release of an acidic pH regulating agent with a relatively slow release rate either sequentially, i.e. after the fast disintegration of the first compressed module, or simultaneously with the fast disintegration of the first compressed module, the acidic pH regulating agent induces a reduction in pH from the above 7.5 induced by the first compressed module.

The reduction in oral pH from above 7.5 to below 7.5, such as below 7.0 facilitates that the fraction of unprotonated, unabsorbed nicotine being present after the first period of use is reduced, as more unabsorbed nicotine is protonated due to the pH reduction.

It is thus understood, that the acidic pH regulating agent is an acidifying agent, which facilitates a reduction in oral pH, i.e. the acidic pH regulating agent will cause an acidification of the oral cavity and protonation of unabsorbed nicotine, thereby reducing the burning sensation.

In some embodiments, the acidic pH regulating agent induces a reduction in oral pH, i.e. in oral saliva, from above 7.5 to below 7.5, including to the neutral area around of between 6.5 and 7.5.

In some embodiments, the acidic pH regulating agent induces a reduction in oral pH to below 7.

In other embodiment, the acidic pH regulating agent induces a reduction in oral pH from above 7.5 to below 7.0.

In advantageous embodiments, the acidic pH regulating agent, when added to water having a pH of 7.0 at a temperature of 25 degrees Celsius will induce a pH below 7.0 when measured at 25 degrees Celsius and atmospheric pressure.

In some embodiments, the acidic pH regulating agent will induce an oral pH below 7.0.

The reduction in oral pH from above 7.5 to below 7.0 facilitates that the fraction of unprotonated, unabsorbed nicotine being present after the first period of use is reduced, as more unabsorbed nicotine is protonated due to the pH reduction.

In some embodiments, the acidic pH regulating agent will induce an oral pH below 6.5.

By providing a tablet comprising an acidic pH regulating agent in a second module, which releases its components over minutes, the undesirable burning sensation was found to be reduced. It is believed, that it is the unprotonated, unabsorbed nicotine, which is causing the burning sensation. By providing a nicotine tablet, facilitating onset of release of an acidic pH regulating agent with a relatively slow release rate either sequentially, i.e. after the fast disintegration of the first compressed module, or simultaneously with the fast disintegration of the first compressed module, the fraction of unprotonated, unabsorbed nicotine being present after the first period of use is reduced, i.e. the unabsorbed nicotine is protonated.

In a sequential release, such as a release from a tablet comprising a core surrounded by a compressed FDT-module, the majority of the alkaline pH regulating agent released from the FDT-module, may gradually disappear from the oral cavity via the saliva being swallowed. The acidic pH regulating agent will start releasing from the core after disintegration of the first compressed module, and will cause an acidification of the oral cavity and protonation of unabsorbed nicotine, thereby reducing the burning sensation. It is noted, that for a tablet design facilitating sequential release from the modules, some degree of overlap in the releasing periods of the first module and the second module may appear, such as in cases where the first compressed module disintegrates unevenly during use and a part of the second compressed module is exposed to the surface prior to complete disintegration of the first compressed module.

In a simultaneous release, such as a release from a bi-layered tablet, the two layers will start releasing simultaneously. The majority of the alkaline pH regulating agent released from the FDT-layer will gradually disappear from the oral cavity via the saliva being swallowed. The lozenge-layer will start releasing the acidic pH regulating agent simultaneously with the FDT-layer, i.e. upon oral administration, however with a much lower release rate and will cause an acidification of the oral cavity and protonation of unabsorbed nicotine kicking in after the first period of use, thereby reducing the burning sensation.

The idea of combining two structurally differently designed modules, one module containing nicotine, makes it possible to provide a fast releasing nicotine tablet, while also providing a tablet facilitating increased pleasure, such as reduced burning and improved taste, in combination with an impressive effect to a user.

The first compressed module is typically designed to disintegrate in less than 60 seconds upon oral administration in the nicotine tablet.

Fast dissolving tablets represent an ideal way of providing the nicotine user with a fast dose/burst of nicotine giving fast effect. However, undesired side effects may occur in case of too high nicotine load delivered too fast. Also, this fast craving relief does not fully cover the pleasure often associated with desired pleasure for the nicotine user.

A prolonged pleasure sensation may thus be obtained by merging the fast craving relief sensation with a second phase sensation into one tablet.

It is however surprising that the desired effects i.e. nicotine craving relief, taste and/or pleasure, such as reduced burning, as perceived by the user, may be obtained in one tablet comprising at least two modules engineered to provide these desired effects.

User time of the tablet may be easily designed to by around 5 minutes, i.e. similar to smoking a cigarette. The bitter taste of nicotine and the undesirable burning sensation may be reduced.

In an advantageous embodiment of the invention the second module provides desirable pleasure sensation by reducing the burning sensation, while at the same time the first module provides a very fast release of nicotine and alkaline pH regulating agent at a concentration ensuring craving relief.

The combination of an FDT-module with a lozenge-module facilitates the manufacture of robust tablets, providing both a fast release of nicotine and a prolonged release of masking compounds while at the same time prolonging an invoked salivation during use of the tablet. The prolonged invoked salivation is believed to assist in the reduced burning sensation as an increased salivation assists the distribution of the acidic pH regulating agent both within the oral cavity and also in the throat upon swallowing.

In an advantageous embodiment of the invention, the water-dissolvable nicotine tablet comprises nicotine in an amount of at least 0.2 mg, such as at least 0.5 mg, such as at least 1.0 mg.

In an advantageous embodiment of the invention, the nicotine water-dissolvable nicotine tablet comprises nicotine in an amount of between 0.2 mg and 5.0 mg of nicotine, such as between 0.5 mg and 4.0 mg of nicotine, such as between 1.0 mg and 3.0 mg of nicotine, such as between 1.0 and 2.0 mg.

In an advantageous embodiment of the invention, the nicotine is comprised in the first compressed module.

In an embodiment of the invention, the first compressed module comprises nicotine in an amount of between 0.2 mg and 5.0 mg of nicotine, such as between 0.5 mg and 4.0 mg of nicotine, such as between 1.0 mg and 3.0 mg of nicotine, such as between 1.0 and 2.0 mg.

In an embodiment of the invention, the first compressed module comprises nicotine in an amount of less than 5% by weight of the first compressed module, such as less than 3% by weight of the first compressed module, such as less than 2% by weight of the first compressed module.

An advantage of the invention may be that a surprisingly effective craving relief is obtained. By providing a first compressed module being an FDT-module comprising nicotine, the tablet of the invention facilitates fast action of nicotine, but at the same time has been shown to provide a sustained craving relief by facilitating a desirable sustained pleasure sensation, which is very effective. Having a very effective craving relief may further provide that the necessary nicotine dose of the tablet, without compromising the resulting effect, may be reduced. A lower nicotine dose may in tern result in a reduction in production cost, as nicotine may be relatively expensive, but may also assist users who want to lower their intake of nicotine.

In an embodiment of the invention, the first compressed module comprises nicotine in an amount of between 0.2 to 5% by weight of the first compressed module, such as 0.3 to 3% by weight of the first compressed module, such as 0.5 to 2% by weight of the first compressed module.

In an embodiment of the invention, wherein the second compressed module is free of nicotine.

An advantage of the present invention is, that by providing a first compressed module being an FDT-module comprising nicotine and an alkaline pH regulating agent, the tablet of the invention facilitates fast action of nicotine and craving relief. Furthermore, the tablet was found provide a sustained craving relief by facilitating a desirable sustained pleasure sensation, which is very effective. Hence, an acceptable craving relief may be achieved from a tablet comprising nicotine only in the first compressed module. Also, by providing a tablet with a second compressed module being free of nicotine, the burning sensation is reduced.

Thus, in the above embodiment, the nicotine is comprised in the first compressed module, such as an embodiment where the tablet consists of the first and second compressed module, the first compressed module comprises the nicotine.

In an embodiment of the invention, the nicotine is comprised in the first compressed module.

In an advantageous embodiment of the invention, the nicotine is selected from the list consisting of nicotine free base and nicotine salts, or combinations thereof.

In an advantageous embodiment of the invention, the nicotine comprises nicotine free base.

Free base nicotine includes nicotine mixed with sugar alcohols, modified calcium carbonate, water-soluble fibers, water-insoluble fibers, and combinations thereof.

In an embodiment of the invention, the nicotine is nicotine free base.

In an advantageous embodiment of the invention, the nicotine comprises nicotine salt.

An advantage of the above embodiment may be that a fast craving relief of nicotine may be facilitated, e.g. due to a fast dissociation of the nicotine salt.

In an advantageous embodiment of the invention, the nicotine is a nicotine salt.

In an advantageous embodiment of the invention, the nicotine salt is selected from the list consisting of nicotine ascorbate, nicotine aspartate, nicotine benzoate, nicotine monotartrate, nicotine bitartrate, nicotine hydrochloride, nicotine dihydrochloride, nicotine citrate, nicotine fumarate, nicotine gensitate, nicotine lactate, nicotine mucate, nicotine laurate, nicotine levulinate, nicotine malate, nicotine perchlorate, nicotine pyruvate, nicotine salicylate, nicotine sorbate, nicotine succinate, nicotine zinc chloride, nicotine sulfate, nicotine tosylate, and combinations thereof.

It is understood that the nicotine salt may also be provided as a hydrated salt.

In an embodiment of the invention, the nicotine salt is selected from the list consisting of nicotine aspartate, nicotine benzoate, nicotine monotartrate, nicotine bitartrate, nicotine hydrochloride, nicotine dihydrochloride, nicotine citrate, nicotine fumarate, nicotine lactate, nicotine mucate, nicotine laurate, nicotine levulinate, nicotine malate, nicotine pyruvate, nicotine sorbate, nicotine succinate, nicotine sulfate, and combinations thereof.

In an embodiment of the invention, the nicotine salt is selected from the list consisting of nicotine benzoate, nicotine monotartrate, nicotine bitartrate, nicotine hydrochloride, nicotine dihydrochloride, nicotine lactate, nicotine malate, nicotine pyruvate, nicotine succinate, and combinations thereof.

In an advantageous embodiment of the invention, the nicotine comprises nicotine bitartrate.

An advantage of the above embodiment may be that a fast craving relief of nicotine may be facilitated, e.g. due to a fast dissociation of nicotine bitartrate.

In an advantageous embodiment of the invention, the nicotine is nicotine bitartrate.

In an advantageous embodiment of the invention, the first compressed module comprises alkaline pH regulating agent in an amount of at least 0.2% by weight of the first compressed module, such as at least 0.3% by weight of the first compressed module, such as at least 0.4% by weight of the first compressed module, such as at least 0.5% by weight of the first compressed module.

The amount of alkaline pH regulating agent should facilitate a desirable pH of above 7.5 in the oral cavity, such as a pH in between 7.5 and 10, such as a pH in between 7.5 and 9.5, such as a pH in between 7.5 and 9.0.

A desirable high pH facilitates absorption of nicotine over the oral mucosa, thus the oral pH is ideally above 7.5 during at least the first 60 seconds of use, such as between 7.5 and 9.0 during at least the first 60 seconds of use or above 7.5 at least during the disintegration time of the first compressed module, such as between 7.5 and 9.0 during the disintegration time of the first compressed module.

The alkaline pH regulating agent released from the FDT-module will dissolve in the saliva and increase the pH in the oral cavity, and thereafter be carried away from the oral cavity via the saliva being swallowed. Thus, the amount of alkaline pH regulating agent, even if excessive amounts are included in the first module, does not interfere with the desired achieved effect from the acidic pH regulating agent released from the second compressed module, i.e. protonation of unabsorbed, unprotonated nicotine.

Also, the high pH value obtained may advantageously provide for a tingling sensation in the mouth which may be perceived as a desirable mouthfeel, e.g. due to resemblance with tobacco-based products.

In an embodiment of the invention, the first compressed module comprises alkaline pH regulating agent in an amount of no more than 10% by weight of the first compressed module, such as no more than 7% by weight of the first compressed module, such as no more than 6% by weight of the first compressed module, such as no more than5% by weight of the first compressed module, such as no more than 3% by weight of the first compressed module, such as no more than 2% by weight of the first compressed module.

Some alkaline pH regulating agents have a distinct taste and, thus may induce an undesirable off-notes to the taste or flavor profile of the tablet. Hence, it may be desirable to not include too much alkaline pH regulating agent, such as no more than 10% by weight of the first compressed module. Also, a too high amount of alkaline pH regulating agent may cause irritation within the oral cavity.

In an advantageous embodiment of the invention, the first compressed module comprises alkaline pH regulating agent in an amount of 0.2 to 10% by weight of the first compressed module, such as 0.2 to 7% by weight of the first compressed module, such as 0.2 to 6% by weight of the first compressed module, such as 0.2 to 5% by weight of the first compressed module, such as 0.3 to 4% by weight of the first compressed module, such as 0.4 to 3% by weight of the first compressed module, such as 0.5 to 2% by weight of the first compressed module.

In an embodiment of the invention, the first compressed module comprises alkaline pH regulating agent in an amount of between 0.5 mg and 30 mg, such as between 1 mg and 20 mg, such as between 5 and 15 mg.

It is understood that the pH regulating effect of the first compressed module should be alkaline. Thus, any embodiments, where some amount of acidic pH regulating agent and an excess amount of alkaline pH regulating agent are included in the first compressed module to provide an overall alkaline effect, are considered within the scope of the present invention.

However, in the interest of compound economy, it may be advantageous to have a first compressed module being free of acidic pH regulating agent.

In an embodiment of the invention, the first compressed module is free of acidic pH regulating agent.

In an advantageous embodiment of the invention, the acidic pH regulating agent is comprised in the second compressed module.

In an advantageous embodiment of the invention, the alkaline pH regulating agent comprises alkaline pH regulating agent selected from the group consisting of sodium carbonate, sodium bicarbonate, potassium carbonate, potassium bicarbonate, trometamol, amino acids, di-alkali hydrogen phosphate, tri-alkali phosphate, or any combination thereof.

In an embodiment of the invention, the alkaline pH regulating agent is selected from the group consisting of sodium carbonate, sodium bicarbonate, potassium carbonate, potassium bicarbonate, trometamol, amino acids, disodium hydrogen phosphate, dipotassium hydrogen phosphate, trisodium phosphate, tripotassium phosphate, or any combination thereof.

In an embodiment of the invention, the alkaline pH regulating agent is selected from the group consisting of Sodium carbonate, Sodium bicarbonate, Potassium carbonate, Potassium bicarbonate, trometamol, amino acids, or any combination thereof.

In an advantageous embodiment of the invention, the alkaline pH regulating agent is selected from the group consisting of Sodium carbonate, Sodium bicarbonate, Potassium carbonate, Potassium bicarbonate, or any combination thereof.

Combinations of a carbonate and a bicarbonate may be especially advantageous. Such combination may e.g. be a sodium carbonate—sodium bicarbonate buffer system, e.g. sodium carbonate and sodium bicarbonate in a weight-ratio between 5:1 and 2.5:1, preferably in a weight-ratio between 4.1:1 and 3.5:1.

In an advantageous embodiment of the invention the pH regulating agent comprises or is sodium carbonate.

In an embodiment of the invention, the alkaline pH regulating agent is selected from the group consisting of trometamol, amino acids, disodium hydrogen phosphate, dipotassium hydrogen phosphate, trisodium phosphate, tripotassium phosphate, or any combination thereof.

In an embodiment of the invention, the alkaline pH regulating agent is selected from the group consisting of trometamol, disodium hydrogen phosphate, dipotassium hydrogen phosphate, trisodium phosphate, tripotassium phosphate, or any combination thereof.

In an embodiment of the invention, the alkaline pH regulating agent comprises di-alkali hydrogen phosphate and/or tri-alkali phosphate, such as disodium phosphate, dipotassium phosphate, trisodium phosphate and/or tripotassium phosphate.

Trometamol and phosphate buffers have a desirable relative neutral taste, hence the use of these pH regulating agents may be found not compromise the taste and mouthfeel of the nicotine tablet.

In an embodiment of the invention, the alkaline pH regulating agent comprises trometamol.

In an embodiment of the invention, the alkaline pH regulating agent consist trometamol.

In the present context the term trometamol refers to (tris(hydroxymethyl)aminomethane), also sometimes referred to as tris buffer.

In an embodiment of the invention, the alkaline pH regulating agent comprises amino acid.

In an embodiment of the invention, the alkaline pH regulating agent consist of amino acid.

In an advantageous embodiment of the invention, the first compressed module induces a pH higher than 7.5 upon dissolution in water having a pH of 7.0, when measured at 25 degrees Celsius and atmospheric pressure.

In an advantageous embodiment of the invention, the first compressed module comprises disintegrant in an amount of at least 0.5% by weight of the first compressed module, such as at least 1% by weight of the first compressed module, such as at least 2% by weight of the first compressed module, such as at least 3% by weight of the first compressed module, such as at least 4% by weight of the first compressed module, such as at least 5% by weight of the first compressed module.

In an advantageous embodiment of the invention, the first compressed module comprises disintegrant in an amount of between 0.5% and 25% by weight of the first compressed module, such as between 0.5% and 15%, such as between 5 and 15%, such as between 5 and 10%.

In an embodiment of the invention, the first compressed module comprises disintegrant in an amount of between 0.5% and 25% by weight of the first compressed module, such as between 5% and 25%, such as between 10 and 25%, such as between 10 and 20%.

In an embodiment of the invention, the first compressed module comprises super disintegrant in an amount of between 0.5% and 25% by weight of the first compressed module, such as between 0.5% and 15%, such as between 5 and 15%, such as between 5 and 10%.

In an embodiment of the invention, the disintegrant has a particle size below 125 micrometers, such as below 75 micrometers, such as below 50 micrometers.

It is understood, that a particle size below 125 micrometers refer to particles able to pass trough a sieve with 120 mesh dimension (US standard mesh), a particle size below 75 micrometers refer to particles able to pass trough a sieve with 200 mesh dimension (US standard mesh), a particle size below 50 micrometers refer to particles able to pass trough a sieve with 325 mesh dimension (US standard mesh), a particle size below 15 micrometers refer to particles able to pass trough a sieve with 800 mesh dimension (US standard mesh).

An advantage of the above embodiment of using disintegrant with a smaller particle size facilitates a shorter disintegration time, e.g. due to a larger relative surface of the disintegrant particles.

Furthermore, the use of disintegrant with a particle size below 125 micrometers improves the mouthfeel of the tablet in use. The fast disintegration of the first compressed module comprising disintegrant with a particle size below 125 micrometer does not cause a sandy sensation or a lumpy sensation within the mouth of the user.

In an embodiment of the invention, at least 50% by weight of the disintegrant has a particle size below 50 micrometers.

In an embodiment of the invention, at least 25% by weight of the disintegrant has a particle size below 15 micrometers.

In an advantageous embodiment of the invention, the disintegrant is selected from the list consisting of starch, pregelatinated starch, cellulose, modified cellulose, microcrystalline cellulose, alginates, ion-exchange resin, calcium silicate, crosslinked cellulose, crosslinked polyvinyl pyrrolidone, crosslinked starch, crosslinked alginic acid, and combinations thereof.

In the present context starch refer to starches of various origin such as potato starch, corn starch, wheat starch, pea starch etc.

Examples of pregelatinized starch disintegrants include structure and brands names such as pregelatinized potato starch, pregelatinized wheat starch, pregelatinized corn starch, Lycatab®, starch 1500® etc.

Examples of modified cellulose disintegrants include structure names such as methyl cellulose, carboxymethyl cellulose, hydroxypropyl cellulose, hydroxypropyl methylcellulose etc.

Microcrystalline cellulose is a refined form of natural cellulose. Examples of microcrystalline cellulose disintegrants include brands names such as Avicel®, Emcocel®, Vivapor® MCC etc.

Examples of alginic acid disintegrants include various alkali alginates and brands names such as Vivapur® alginate etc.

It is understood that some disintegrant are referred to as super disintegrants.

In an advantageous embodiment of the invention, the disintegrant comprises a super disintegrant.

In some embodiment, the disintegrant may comprise combination of regular disintegrant and super-disintegrant.

In an advantageous embodiment of the invention, the disintegrant is a super disintegrant.

In an advantageous embodiment of the invention, the disintegrant is a super disintegrant selected from the group consisting of crosslinked cellulose, crosslinked polyvinyl pyrrolidone, crosslinked starch, crosslinked alginic acid, and any combinations thereof.

Examples of crosslinked cellulose super disintegrants include structure and brands names such as Croscarmellose®, L-HPC, Solutab® etc.

Examples of crosslinked polyvinyl pyrrolidone (PVP) super disintegrants include structure and brands names such as Crosspovidone M®, Kollidon®, Polyplasdone®, polyplasdone XL®, Kollidon CL® etc.

Examples of crosslinked starch super disintegrants include structure and brands names such as sodium starch glycolate, Glycolys®, Explotab®, Primogel®, Vivastar®, Tablo® etc.

Examples of cross linked alginic acid include structure and brands names such as Alginic acid NF®, Staialgine® etc.

In an embodiment of the invention, the disintegrant is a super disintegrant selected from the group consisting of crosslinked cellulose, crosslinked polyvinyl pyrrolidone (PVP), crosslinked starch, and any combinations thereof.

In an embodiment of the invention, the first compressed module comprises super disintegrant selected from the group consisting of crosslinked cellulose, crosslinked polyvinyl pyrrolidone, crosslinked starch, crosslinked alginic acid, and any combinations thereof, in an amount of between 0.5% and 25% by weight of the first compressed module, such as between 0.5% and 15%, such as between 5 and 15%, such as between 5 and 10%.

In an advantageous embodiment of the invention, the super disintegrant is crosslinked polyvinyl pyrrolidone (PVP).

In an embodiment of the invention, at least 50% by weight of the crosslinked polyvinyl pyrrolidone (PVP) has a particle size below 50 micrometers.

In an embodiment of the invention, at least 25% by weight of the crosslinked polyvinyl pyrrolidone (PVP) has a particle size below 15 micrometers.

An advantage of using cross-linked polyvinylpyrrolidone as super disintegrant, may be that it decreases the dependence of the disintegration time on the compression force while allowing rather low disintegration times even when using high compression forces.

In an embodiment of the invention, the disintegrant is a non-ionic disintegrant.

In an embodiment of the invention the disintegrant is a non-ionic super-disintegrant, such as crosslinked polyvinyl pyrrolidone (PVP).

In an embodiment of the invention, the first compressed module has a water content of less than 10% by weight, such as less than 5% by weight, such as less than 2% by weight, such as less than 1% by weight.

In an embodiment of the invention, the first compressed module has a water content of 0-10% by weight, such as 0.01-5% by weight, such as 0.05-2% by weight, such as 0.1 — 1% by weight.

I.e. in the above embodiments, the first compressed module may be free of water.

An advantage of the above embodiment may be that stability of the first compressed module is increased. This is in particular when the first compressed module comprises disintegrant, such as super disintegrant.

In an advantageous embodiment of the invention, the second compressed module comprises acidic pH regulating agent in a molar ratio of at most 10 relative to the nicotine in the first compressed module, such as at most 8 relative to the nicotine in the first compressed module, such as at most 7 relative to the nicotine in the first compressed module, such as at most 6 relative to the nicotine in the first compressed module,. Such as at most 5 relative to the nicotine in the first compressed module, such as at most 3 relative to the nicotine in the first compressed module.

By providing a tablet releasing acidic pH regulating agent from the second module, the pH within the oral cavity is acidified and unabsorbed, unprotonated nicotine is protonated. It has been found that this correlates with a reduced burning sensation as demonstrated in example 3C and 3D.

If a desirable amount of acidic pH regulating agent is included in the tablet, the acidic pH regulating agent may also be found to improve or support the taste or flavor profile of the tablet, thereby also improving the overall pleasure sensation of the tablet. This may typically be the case when fruit flavors are used.

However, including a too high amount of acidic pH regulating agent might compromise the taste and flavor of the tablet and thereby compromise the overall pleasure sensation.

Here, the molar ratio refers to the molar content of acidic pH regulating agent divided by the molar content of nicotine.

In an advantageous embodiment of the invention, the second compressed module comprises acidic pH regulating agent in a molar ratio of at least 0.5 relative to the nicotine in the first compressed module, such as at least 0.75 relative to the nicotine in the first compressed module, such as at least 1 relative to the nicotine in the first compressed module, such as at least 2 relative to the nicotine in the first compressed module.

The nicotine and the alkaline pH regulating agent are released from the first compressed module, whereby a significant amount of the nicotine is absorbed, such as about 50% of the nicotine is absorbed, such as about 60% of the nicotine is absorbed, such as about 70% of the nicotine is absorbed, such as about 80% of the nicotine is absorbed, or even more. Hence, the amount of acidic pH regulating agent in the second module should be matched with the effect of the first compressed module, i.e. the first compressed module is engineered to provide a high nicotine absorption, i.e. craving relief, and the second compressed module is engineered to both prolong the effect of the first compressed module, i.e. to facilitate a sustained craving relief, and to reduce the side-effects of the effect of the first compressed module, i.e. to reduce burning sensation and increase pleasure sensation.

An excess amount of acidic pH regulating agent may advantageously be added in order to accommodate for an amount of the acidic pH regulating agent reacting with other components than unabsorbed nicotine within the oral cavity, such as saliva components, alkaline pH regulating agent etc., i.e. an excess amount may advantageously be added in order to ensure an effective amount being available for protonation of any unabsorbed nicotine.

Also, the second compressed module has a lower release rate than the first compressed module, hence the effect of the acidic pH regulating agent, i.e. acidification of the oral cavity and protonation of nicotine, may be achieved faster if higher amounts of acid, such as excess amounts relative to the nicotine, is included in the tablet.

Furthermore, the acidic pH regulating agent may in some embodiments enhance the flavor of the tablet.

In an advantageous embodiment of the invention, the second compressed module comprises acidic pH regulating agent in a molar ratio of between 0.5 and 10 relative to the nicotine in the first compressed module, such as between 0.75 and 8 relative to the nicotine in the first compressed module, such as between 0.75 and 7 relative to the nicotine in the first compressed module, such as between 1 and 6 relative to the nicotine in the first compressed module.

In an embodiment of the invention, the first compressed module comprises pH regulating agent in an amount of 0.2 to 10% by weight of the first compressed module, such as 0.2 to 7% by weight of the first compressed module, such as 0.2 to 6% by weight of the first compressed module, such as 0.2 to 5% by weight of the first compressed module, such as 0.3 to 4% by weight of the first compressed module, such as 0.4 to 3% by weight of the first compressed module, such as 0.5 to 2% by weight of the first compressed module, and the second compressed module comprises acidic pH regulating agent in a molar ratio of between 0.5 and 10 relative to the nicotine in the first compressed module, such as between 0.75 and 8 relative to the nicotine in the first compressed module, such as between 0.75 and 7 relative to the nicotine in the first compressed module, such as between 1 and 6 relative to the nicotine in the first compressed module.

In an embodiment of the invention, the second compressed module comprises acidic pH regulating agent in an amount of no more than 15% by weight of the second compressed module, such as no more than 10% by weight of the second compressed module, such as no more than 5% by weight of the second compressed module.

In an embodiment of the invention, the second compressed module comprises acidic pH regulating agent in an amount of 0.5-15% by weight of the second compressed module, such as 0.5-10% by weight of the second compressed module, such as 0.5-5% by weight of the second compressed module, such as 0.5-3% by weight of the second compressed module.

In an embodiment of the invention, the first compressed module comprises pH regulating agent in an amount of 0.2 to 10% by weight of the first compressed module, such as 0.2 to 7% by weight of the first compressed module, such as 0.2 to 6% by weight of the first compressed module, such as 0.2 to 5% by weight of the first compressed module, such as 0.3 to 4% by weight of the first compressed module, such as 0.4 to 3% by weight of the first compressed module, such as 0.5 to 2% by weight of the first compressed module, and the second compressed module comprises acidic pH regulating agent in an amount of 0.5-15% by weight of the second compressed module, such as 0.5-10% by weight of the second compressed module, such as 0.5-5% by weight of the second compressed module, such as 0.5-3% by weight of the second compressed module.

In an embodiment of the invention, the second compressed module comprises acidic pH regulating agent in an amount of no more than 30 mg, such as no more than 25 mg, such as no more than 20 mg, such as no more than 15 mg, such as no more than 10 mg.

In an advantageous embodiment of the invention, the second compressed module comprises acidic pH regulating agent in an amount of between 0.5 mg and 30 mg, such as between 1 mg and 20 mg, such as between 5 and 15 mg.

In an embodiment of the invention, the first compressed module comprises nicotine in an amount of between 0.2 mg and 5.0 mg, alkaline pH regulating agent in an amount of between 0.5 mg and 30 mg, such as between 1 mg and 20 mg, such as between 5 and 15 mg, and the second compressed module comprises acidic pH regulating agent in an amount of between 0.5 mg and 30 mg, In an embodiment of the invention, the acidic pH regulating agent has at least one pKa value at 25 degrees Celsius being below 7, such as below 6, such as below 5.

In an advantageous embodiment of the invention, the acidic pH regulating agent comprises acidic pH regulating agent selected from the list consisting of phosphoric acid, mono-alkali dihydrogen phosphate, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the second compressed module comprises acidic pH regulating agent in a molar ratio of at least 0.5 relative to the nicotine in the first compressed module, and the acidic pH regulating agent comprises acidic pH regulating agent selected from the list consisting of phosphoric acid, mono-alkali dihydrogen phosphate, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the second compressed module comprises acidic pH regulating agent in a molar ratio of between 0.5 and 10 relative to the nicotine in the first compressed module, and the acidic pH regulating agent comprises acidic pH regulating agent selected from the list consisting of phosphoric acid, mono-alkali dihydrogen phosphate, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

Thus, the molar ratio refers to the molar amount of acidic pH regulating agent relative to the molar amount of nicotine in the first compressed module.

In an embodiment of the invention, the first compressed module comprises nicotine in an amount of between 0.2 mg and 5.0 mg of nicotine, the nicotine is selected from the list consisting of nicotine free base and nicotine salts, or combinations thereof, and the second compressed module comprises acidic pH regulating agent in a molar ratio of between 0.5 and 10 relative to the nicotine in the first compressed module.

In an embodiment of the invention, the first compressed module comprises nicotine in an amount of between 0.2 mg and 5.0 mg of nicotine, the nicotine is nicotine salts, and the second compressed module comprises acidic pH regulating agent in a molar ratio of between 0.5 and 10 relative to the nicotine in the first compressed module, and the acidic pH regulating agent comprises acidic pH regulating agent selected from the list consisting of phosphoric acid, mono-alkali dihydrogen phosphate, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the acidic pH regulating agent comprises acidic pH regulating agent selected from the list consisting of phosphoric acid, monosodium dihydrogen phosphate, monopotassium dihydrogen phosphate, citric acid, monosodium dihydrogen citrate, monopotassium dihydrogen citrate, disodium hydrogen citrate, dipotassium hydrogen citrate, malic acid, monosodium malate, monopotassium malate, succinic acid, monosodium succinate, monopotassium succinate, tartaric acid, monosodium tartrate, monopotassium tartrate, acetic acid, sorbic acid, benzoic acid, formic acid, and combinations thereof.

In an embodiment of the invention, the acidic pH regulating agent is selected from the list consisting of phosphoric acid, mono-alkali dihydrogen phosphate, mono-alkali dihydrogen phosphate—di-alkali hydrogen phosphate mixture, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the second compressed module comprises acidic pH regulating agent in a molar ratio of at least 0.5 relative to the nicotine in the first compressed module, and the acidic pH regulating agent comprises acidic pH regulating agent selected from the list consisting of phosphoric acid, mono-alkali dihydrogen phosphate, mono-alkali dihydrogen phosphate—di-alkali hydrogen phosphate mixture, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In embodiments, where the acidic pH regulating agent is mixture of pH regulating agents, the molar ratio refers to the total molar amount of acidic pH regulating agent(s) relative to the molar amount of nicotine in the first compressed module.

In an advantageous embodiment of the invention, the acidic pH regulating agent is selected from the list consisting of phosphoric acid, mono-alkali dihydrogen phosphate, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the acidic pH regulating agent is selected from the list consisting of phosphoric acid, monosodium dihydrogen phosphate, monopotassium dihydrogen phosphate, citric acid, monosodium dihydrogen citrate, monopotassium dihydrogen citrate, disodium hydrogen citrate, dipotassium hydrogen citrate, malic acid, monosodium malate, monopotassium malate, succinic acid, monosodium succinate, monopotassium succinate, tartaric acid, monosodium tartrate, monopotassium tartrate, acetic acid, sorbic acid, benzoic acid, formic acid, and combinations thereof.

In an embodiment of the invention, the acidic pH regulating agent is selected from the list consisting of citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the acidic pH regulating agent is selected from the list consisting of citric acid, monosodium dihydrogen citrate, monopotassium dihydrogen citrate, disodium hydrogen citrate, dipotassium hydrogen citrate, malic acid, monosodium malate, monopotassium malate, succinic acid, monosodium succinate, monopotassium succinate, tartaric acid, monosodium tartrate, monopotassium tartrate, acetic acid, sorbic acid, benzoic acid, formic acid, and combinations thereof.

In an advantageous embodiment of the invention, the acidic pH regulating agent is selected from the list consisting of citric acid, mono-alkali dihydrogen citrate, di-alkali hydrogen citrate, malic acid, mono-alkali malate, and combinations thereof.

In an embodiment of the invention, the acidic pH regulating agent is selected from the list consisting of citric acid, monosodium dihydrogen citrate, monopotassium dihydrogen citrate, disodium hydrogen citrate, dipotassium hydrogen citrate, malic acid, monosodium malate, monopotassium malate, and combinations thereof.

In an embodiment of the invention, the acidic pH regulating agent is phosphoric acid, mono-alkali dihydrogen phosphate, or combinations thereof.

In an embodiment of the invention, the second compressed module induces a pH lower than 7.5 upon dissolution in water having a pH of 7.0, when measured at 25 degrees Celsius and atmospheric pressure.

It is understood that the pH regulating effect of the second compressed module should be acidifying relative to the pH induced by the first compressed module. The acidic pH regulating agent(s) of the second compressed module should provide a reduced oral pH upon dissolution, i.e. the second compressed module should provide a reduction in oral pH from above 7.5 induced by the first compressed module to below 7.5. Hence, the second compressed module induces a pH lower than 7.5, when added to water at a pH of 7.0, when measured at 25 degrees Celsius and atmospheric pressure.

In an embodiment of the invention, the second compressed module induces a pH lower than 7.0 upon dissolution in water having a pH of 7.0, when measured at 25 degrees Celsius and atmospheric pressure.

In preferred embodiments of the invention, it is understood, that the pH regulating effect of the second compressed module should be acidic. In preferred embodiments of the invention, the pH regulating agents of the second compressed module should provide a lower pH when added to water at a pH of 7.0, when measured at 25 degrees Celsius and atmospheric pressure. Thus, any embodiments, where some amount of alkaline pH regulating agent and an excess amount of acidic pH regulating agent are included in the second module to provide an overall acidic effect, are considered within the scope of the present invention.

However, in the interest of compound economy, it may be advantageous to have a second compressed module being free of alkaline pH regulating agent.

In some embodiments, the acidic pH regulating agent, when added to water having a pH of 7.0 at a temperature of 25 degrees Celsius will induce a pH below 7.0, whereas the alkaline pH regulating agent, when added to water having a pH of 7.0 will induce a pH above 7.5.

In an embodiment of the invention, the second compressed module is free of alkaline pH regulating agent.

In an advantageous embodiment of the invention, the alkaline pH regulating agent is comprised in the first compressed module.

In an advantageous embodiment of the invention, the nicotine tablet comprises flavor.

The flavor may advantageously be used as taste masking for the nicotine.

In an embodiment of the invention, the nicotine tablet comprises flavor in an amount of at least 0.1% by weight of the nicotine tablet.

In an advantageous embodiment of the invention, the nicotine tablet comprises flavor in an amount of 0.1 to 15.0% by weight of the nicotine tablet, such as 0.1 to 10.0% by weight of the nicotine tablet, such as 0.1 to 5.0% by weight of the nicotine tablet, such as 0.2 to 3.0% by weight of the nicotine tablet.

In an embodiment of the invention, the flavor is comprised in the first and second compressed modules, i.e. both modules comprise flavor.

In an embodiment of the invention, the second compressed module comprises flavor.

In an advantageous embodiment of the invention, the flavor is comprised in the second compressed module.

In an embodiment of the invention, the second compressed module comprises flavor in an amount of 0.1 to 15.0% by weight of the second compressed module, such as 0.1 to 10.0% by weight of the second compressed module, such as 0.1 to 5.0% by weight of the second compressed module, such as 0.2 to 3.0% by weight of the second compressed module.

In an advantageous embodiment of the invention, the flavor is comprised in the second compressed module.

Thus, in the above embodiment, all flavor is comprised in the second compressed module, i.e. the first compressed module is free of flavor.

In an embodiment of the invention, where the tablet consists of the first and second compressed module and where all flavor is comprised in the second compressed module, the first compressed module is free of flavor.

In an embodiment of the invention, the first compressed module is free of flavor.

An advantage of the above embodiment may be that nicotine stability is increased by facilitating separation of nicotine from flavor and thereby minimizing any flavor induced degradation of nicotine in the first compressed module. A further advantage of the above embodiment may be that the nicotine tablet is relatively simple to manufacture due to a limited amount of ingredients in each module, while obtaining surprisingly good results with respect to taste and flavor perception for the users.

Flavor may induce salivation during use of the tablet. By only including flavor in the second module, the flavor induced saliva generation may be limited or even avoided, during disintegration of the first compressed module. Thus, the users desire to swallow during disintegration of the first compressed module is diminished, whereby less nicotine will reach the throat and cause burning.

Also, in embodiments where the first and the second compressed modules are tablet layers, such tablet enables simultaneous release of flavor from the second compressed module, while nicotine is released from the first compressed module, whereby the bitter taste of nicotine may be reduced.

In an advantageous embodiment of the invention the flavor is selected from the group of menthol, peppermint, wintergreen, sweet mint, spearmint, vanillin, chocolate, coffee, cinnamon, clove, tobacco, citrus and fruit flavors and mixtures thereof.

In an embodiment of the invention, the nicotine and the flavor are comprised in opposite modules.

In an embodiment of the invention, the first compressed module is free of flavor and wherein the second compressed module is free of nicotine.

An advantage of the above embodiment may be that nicotine stability is increased by facilitating separation of nicotine from flavor and thereby minimizing any flavor induced degradation of nicotine.

In an advantageous embodiment of the invention, the flavor is comprised in the second compressed module and the nicotine is comprised in the first compressed module.

In an embodiment of the invention, the second compressed module comprises fruit flavor and the acidic pH regulating agent is selected from the group consisting of citric acid, mono-alkali dihydrogen citrate, di-alkali hydrogen citrate, malic acid, mono-alkali malate, and combinations thereof.

In an advantageous embodiment of the invention, the nicotine tablet comprises sugar alcohol.

Sugar alcohols may advantageously be used to achieve a desirable taste. Also, sugar alcohols are an attractive alternative to sugar sweeteners.

In an advantageous embodiment of the invention, the nicotine tablet comprises sugar alcohol in an amount of at least 50% by weight of the nicotine tablet, such as at least 60% by weight of the nicotine tablet, such as at least 70% by weight of the nicotine tablet, such as at least 75% by weight of the nicotine tablet, such as at least 80% by weight of the nicotine tablet, at least 85% by weight of the nicotine tablet.

Sugar alcohols have a desirable solubility. Hence, nicotine tablet comprising a significant amount of sugar alcohol was found to facilitate a desirable dissolution of the nicotine tablet.

In an advantageous embodiment of the invention, the nicotine tablet comprises the sugar alcohol in an amount of 50 to 97% by weight of the nicotine tablet, such as 60 to 97% by weight of the nicotine tablet, such as 70 to 97% by weight of the nicotine tablet, such as 70 to 90% by weight of the nicotine tablet.

In an embodiment of the invention, the nicotine tablet comprises the sugar alcohol in an amount of 50 to 97% by weight of the nicotine tablet, such as 60 to 95% by weight of the nicotine tablet, such as 70 to 95% by weight of the nicotine tablet, such as 75 to 95% by weight of the nicotine tablet, such as 80 to 95% by weight of the nicotine tablet, such as 85 to 95% by weight of the nicotine tablet.

In an embodiment of the invention, the first compressed module comprises sugar alcohol.

Sugar alcohols have a desirable saliva solubility. Thus, upon use of the nicotine tablet, the sugar alcohols will dissolve and assist release from the modules, such as fast release of nicotine and alkaline pH regulating agent from the first compressed module, and release of acidic pH regulating agent from the second compressed module.

In an embodiment of the invention, the first compressed module comprises sugar alcohol in an amount of at least 50% by weight of the first compressed module, such as at least 60% by weight of the first compressed module, such as at least 70% by weight of the first compressed module, such as at least 80% by weight of the first compressed module, such as at least 85% by weight of the first compressed module.

In an advantageous embodiment of the invention, the first compressed module comprises sugar alcohol in an amount of 50% to 97% by weight of the first compressed module, such as 60% to 95% by weight of the first compressed module, such as 70% to 90% by weight of the first compressed module.

In an embodiment of the invention, the first compressed module comprises sugar alcohol in an amount of 50 to 97% by weight of the first compressed module, such as 60 to 97% by weight of the first compressed module, such as 70 to 97% by weight of the first compressed module.

In an embodiment of the invention, the first compressed module comprises sugar alcohol in an amount of 75 to 97% by weight of the first compressed module, such as 80 to 97% by weight of the first compressed module, such as 85 to 97% by weight of the first compressed module.

In an embodiment of the invention, the second compressed module comprises sugar alcohol in an amount of at least 50% by weight of the second compressed module, such as at least 60% by weight of the second compressed module, such as at least 70% by weight of the second compressed module, such as at least 80% by weight of the second compressed module, such as at least 85% by weight of the second compressed module, such as at least 90% by weight of the second compressed module.

In an advantageous embodiment of the invention, the second compressed module comprises sugar alcohol in an amount of 50% to 97% by weight of the second compressed module, such as 60% to 95% by weight of the second compressed module, such as 70% to 90% by weight of the second compressed module.

In an embodiment of the invention, the second compressed module comprises sugar alcohol in an amount of 50 to 97% by weight of the second compressed module, such as 60 to 97% by weight of the second compressed module, such as 70 to 97% by weight of the second compressed module.

In an embodiment of the invention, the second compressed module comprises sugar alcohol in an amount of 75 to 97% by weight of the second compressed module, such as 80 to 97% by weight of the second compressed module, such as 85 to 97% by weight of the second compressed module, such as 90 to 97% by weight of the second compressed module.

In an embodiment of the invention, the sugar alcohol is a solid sugar alcohol at 25 degrees Celsius.

The solid sugar alcohols have a desirable compressibility; hence the use of sugar alcohols is desirable when forming compressed tablets.

In an embodiment of the invention, the sugar alcohol is selected from sugar alcohols comprising at least 4 carbon atoms.

In an embodiment of the invention, the tablet is free of sugar alcohols comprising no more than three carbons. Examples of sugar alcohols comprising no more than three carbons include glycerol, propylene glycol, and ethylene glycol.

In an embodiment, the nicotine tablet is free of glycerol.

Compression and fusion of two such different module compositions into a single multi-modular nicotine tablet may not necessarily be trivial as the invention requires a certain design to get the desired effect.

In an advantageous embodiment of the invention, the first and the second compressed modules comprises sugar alcohol.

In an embodiment of the invention, the sugar alcohol is selected from the list consisting of xylitol, maltitol, mannitol, erythritol, isomalt, sorbitol, lactitol or any combination thereof.

In an advantageous embodiment of the invention, the sugar alcohol of the first compressed module is selected from the list consisting of xylitol, maltitol, mannitol, erythritol, isomalt, sorbitol, lactitol or any combination thereof.

In an embodiment of the invention, the first compressed module comprises sugar alcohol in an amount of at least 50% by weight of the first compressed module, such as at least 60% by weight of the first compressed module, such as at least 70% by weight of the first compressed module, such as at least 80% by weight of the first compressed module, such as at least 85% by weight of the first compressed module, wherein the sugar alcohol is selected from the list consisting of xylitol, maltitol, mannitol, erythritol, isomalt, sorbitol, lactitol or any combination thereof.

In an embodiment of the invention, the first compressed module comprises nicotine selected from the list consisting of nicotine free base and nicotine salts, or combinations thereof, alkaline pH regulating agent selected from the group consisting of sodium carbonate, sodium bicarbonate, potassium carbonate, potassium bicarbonate, trometamol, amino acids, disodium hydrogen phosphate, dipotassium hydrogen phosphate, trisodium phosphate, tripotassium phosphate, or any combination thereof.

and sugar alcohol in an amount of at least 50% by weight of the first compressed module, such as at least 60% by weight of the first compressed module, such as at least 70% by weight of the first compressed module, such as at least 80% by weight of the first compressed module, such as at least 85% by weight of the first compressed module, wherein the sugar alcohol is selected from the list consisting of xylitol, maltitol, mannitol, erythritol, isomalt, sorbitol, lactitol or any combination thereof.

An advantage of the above embodiment may be that a fast effect for the user, i.e. craving relief, is obtained, since the nicotine, the alkaline pH regulating agent and the sugar alcohol dissolves relatively fast after disintegration of the first module, whereby efficient nicotine absorption may be achieved.

In an embodiment of the invention, the sugar alcohol of the first compressed module is selected from the list consisting of xylitol, mannitol, erythritol, isomalt, or any combination thereof In an advantageous embodiment of the invention, the sugar alcohol of the second compressed module is selected from the list consisting of xylitol, maltitol, mannitol, erythritol, isomalt, sorbitol, lactitol or any combination thereof.

In an embodiment of the invention, the second compressed module comprises sugar alcohol in an amount of at least 50% by weight of the second compressed module, such as at least 60% by weight of the second compressed module, such as at least 70% by weight of the second compressed module, such as at least 80% by weight of the second compressed module, such as at least 85% by weight of the second compressed module, wherein the sugar alcohol is selected from the list consisting of xylitol, maltitol, mannitol, erythritol, isomalt, sorbitol, lactitol or any combination thereof.

In an embodiment of the invention, the second compressed module comprises acidic pH regulating agent selected from the list consisting of phosphoric acid, mono-alkali dihydrogen phosphate, mono-alkali dihydrogen phosphate—di-alkali hydrogen phosphate mixture, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof, and sugar alcohol in an amount of at least 50% by weight of the second compressed module, such as at least 60% by weight of the second compressed module, such as at least 70% by weight of the second compressed module, such as at least 80% by weight of the second compressed module, such as at least 85% by weight of the second compressed module, wherein the sugar alcohol is selected from the list consisting of xylitol, maltitol, mannitol, erythritol, isomalt, sorbitol, lactitol or any combination thereof.

In an embodiment of the invention, the sugar alcohol of the second compressed module is selected from the list consisting of mannitol, erythritol, isomalt, sorbitol, xylitol, or any combination thereof.

In an embodiment of the invention, the sugar alcohol comprises a DC (direct compressible) grade sugar alcohol.

In an embodiment of the invention, at least 50% by weight of the sugar alcohol is a DC (direct compressible) grade sugar alcohol.

In an embodiment of the invention the nicotine tablet is substantially free of mono- and disaccharides.

In an embodiment of the invention, the nicotine tablet is sugar-free. Thus, in this embodiment, the nicotine tablet does not comprise any sugar.

In an embodiment of the invention the nicotine tablet comprises high intensity sweetener.

In an embodiment of the invention, the high intensity sweetener is selected from sucralose, aspartame, salts of acesulfame, such as acesulfame potassium, alitame, saccharin and its salts, cyclamic acid and its salts, glycyrrhizin, dihydrochalcones, thaumatin, monellin, stevioside, and any combination thereof.

In an embodiment of the invention, the nicotine tablet comprises no more than 0.2% by weight of high intensity sweetener, such as no more than 0.1% by weight of high intensity sweetener.

In an embodiment of the invention, the second compressed module comprises high intensity sweetener.

In an embodiment of the invention, the first compressed module comprises high intensity sweetener.

In an embodiment of the invention, the high intensity sweetener is comprised in the second compressed module.

Thus, in the above embodiment, all high intensity sweetener is comprised in the second compressed module, i.e. the first compressed module is free of high intensity sweetener.

An advantage of this embodiment may be that the nicotine tablet is relatively simple to manufacture due to a limited amount of ingredients in each module, while obtaining surprisingly good results with respect to taste and flavor perception for the users.

In an embodiment of the invention, the high intensity sweetener and flavor are comprised in the second compressed module.

In an embodiment of the invention, the second compressed module comprises binder in an amount of no more than 10% by weight of the second compressed module, such as no more than 8% by weight of the second compressed module, such as no more than 6% by weight of the second compressed module.

Binder may advantageously be added to the second compressed module to obtain a desirable cohesiveness and mechanical strength.

Furthermore, binders may be used to facilitate a disintegration time of more than 2 minutes, whereby the second compressed module provides suitable long-term masking of the nicotine.

Also, the use of a second compressed module being a lozenge module facilitates the manufacture of robust tablets, and providing a prolonged release of masking compounds.

In an advantageous embodiment of the invention, the second compressed module comprises binder in an amount of between 1 and 10% by weight of the second compressed module, such as between 1 and 8% by weight of the second compressed module, such as between 2 and 5% by weight of the second compressed module.

In an advantageous embodiment of the invention, the first compressed module comprises binder in an amount of no more than 5% by weight of the first compressed module, such as no more than 4% by weight of the first compressed module, such as no more than 3% by weight of the first compressed module.

In an advantageous embodiment of the invention, the first compressed module comprises binder in an amount of between 0.5 and 5% by weight of the first compressed module, such as between 0.5 and 4% by weight of the first compressed module, such as between 1 and 3% by weight of the first compressed module.

In an advantageous embodiment of the invention the first compressed module comprises binder in an amount of no more than 5% by weight of the first compressed module and super-disintegrant in an amount of at least 5% by weight of the first compressed module.

The above embodiment may ensure a desirable cohesiveness of the module composition during tableting and a desirable low disintegration time during use of the tablet.

In an embodiment of the invention, the first compressed module constitutes at least 10% by weight of the nicotine tablet, such as at least 20% by weight of the nicotine tablet.

In an advantageous embodiment of the invention, the first compressed module constitutes between 10% to 50% by weight of the nicotine tablet, such as 20% to 40% by weight of the nicotine tablet, such as 10% to 30% by weight of the nicotine tablet, such as 20% to 30% by weight of the nicotine tablet.

In an embodiment of the invention, the second compressed module constitutes at least 50% by weight of the nicotine tablet, such as at least 60% by weight of the nicotine tablet.

In an embodiment of the invention, the second compressed module constitutes between 50% to 90% by weight of the nicotine tablet, such as 50% to 90% by weight of the nicotine tablet, such as 60% to 90% by weight of the nicotine tablet, such as 70% to 90% by weight of the nicotine tablet, such as 70% to 80% by weight of the nicotine tablet, such as 80% to 90% by weight of the nicotine tablet, such as 65% to 75% by weight of the nicotine tablet.

In an embodiment of the invention, the first compressed module encapsulates the second compressed module.

Obtaining a nicotine tablet with a second compressed module encapsulated by a first compressed module may be obtained by applying a press coat as the first compressed module around the second compressed module.

In an advantageous embodiment of the invention, the first compressed module is surrounding the second compressed module being a compressed tablet core.

In an embodiment of the invention, the first compressed module is a compressed coating surrounding the second compressed module being a compressed tablet core.

In an embodiment of the invention, the first compressed module is partially surrounding the second compressed module. It is here understood, that the second compressed module will be partly surrounded by the first compressed module, i.e. the second compressed module will have a partly exposed surface.

In an advantageous embodiment of the invention the first compressed module and second compressed modules are two layers fused by compression.

In an advantageous embodiment of the invention, the first compressed module and the second compressed module are tablet layers.

In is understood here, that tablet module refers to layers having an exposed surface area, such as the first compressed module being a layer having an exposed surface area of maximum 50% of a total exposed surface area of the nicotine tablet, such as 40% of the total exposed surface area of the nicotine tablet, such as 30% of the total exposed surface area of the nicotine tablet.

In an embodiment of the invention, the first compressed module at least partly encapsulates the second compressed module.

In an embodiment of the invention, the first compressed module is a tablet layer having an exposed surface area of maximum 50% of a total exposed surface area of the nicotine tablet, such as 40% of the total exposed surface area of the nicotine tablet, such as 30% of the total exposed surface area of the nicotine tablet.

An advantage of providing a tablet with layers may be that components are released from the layers upon oral administration. Thus, the first compressed module being a fast disintegrating layer will upon oral administration start releasing nicotine and the second compressed module being a lozenge layer will start releasing its components, although with a lower release rate. This may advantageously be used to reduce the burning sensation caused by the nicotine provided in the fast disintegrating layer, by facilitating release of acidic pH regulating agent from the lozenge layer.

Also, this may advantageously be used to mask the bitter taste of nicotine, such a by providing nicotine in the fast disintegrating layer and masking components, such a flavor, in the lozenge layer. Furthermore, it may be used to mask a possible unpleasant alkaline sensation due to the fast release of alkaline pH regulating agent from the fast disintegrating layer, by releasing flavor from the second layer.

In an embodiment of the invention, the nicotine tablet consists of the first compressed module and second compressed module, the first and second compressed modules being two layers fused by compression.

The layers or modules of the nicotine tablet may be formed in many different ways within the scope of the invention. As seen from above, the nicotine tablet may be circular, oval or edged, e.g. square.

In an embodiment of the invention, the compressed first module and the compressed second module are solid modules.

In an advantageous embodiment of the invention, the nicotine tablets consist of solid modules.

Thus, it is understood that a tablet according to the above embodiment, does not comprise liquid or fluid modules, such as a liquid or a fluid center.

In an advantageous embodiment of the invention, the first compressed module and the second compressed module are solid tablet layers.

In an advantageous embodiment of the invention, the first compressed module has a water content of less than 10% by weight, such as less than 5% by weight, such as less than 2% by weight, such as less than 1% by weight.

An advantage of the above embodiment may be that stability of the first compressed module is increased. This is in particular due to the first compressed module comprising disintegrant, such as super disintegrant.

In an embodiment of the invention, the first compressed module has a water content of 0-10% by weight, such as 0.01-5% by weight, such as 0.05-2% by weight, such as 0.1-1% by weight.

I.e. in the above embodiments, the first compressed module may be free of water.

In an embodiment of the invention, the second compressed module has a water content of less than 10% by weight, such as less than 5% by weight, such as less than 2% by weight, such as less than 1% by weight.

In an embodiment of the invention, the second compressed module has a water content of 0-10% by weight, such as 0.01-5% by weight, such as 0.05-2% by weight, such as 0.1-1% by weight.

I.e. in the above embodiments, the second compressed module may be free of water.

In an advantageous embodiment of the invention, the water-dissolvable nicotine tablet has a water content of less than 10% by weight, such as less than 5% by weight, such as less than 2% by weight, such as less than 1% by weight.

In an embodiment of the invention, the water-dissolvable nicotine tablet has a water content of 0-10% by weight, such as 0.01-5% by weight, such as 0.05-2% by weight, such as 0.1-1% by weight.

I.e. in the above embodiments, the water-dissolvable nicotine tablet may be free of water.

In an advantageous embodiment of the invention, the nicotine tablet has a maximum total weight of 1 gram, such as 0.9 gram, such as 0.75 gram, such as 0.5 gram, such as 0.4 gram, such as 0.3 gram.

An advantage of nicotine tablets having a volume below the maximum stated volume is the possibility to use the nicotine tablet discretely. Furthermore, it provides the option of self-titration.

In an advantageous embodiment of the invention, the nicotine tablet has a total weight of 0.2 to 1 gram, such as 0.2 to 0.9 gram, such as 0.2 to 0.75 gram, such as 0.2 to 0.5 gram.

In an embodiment of the invention, the nicotine tablet has a maximum total volume of 0.7 cm3, such as 0.6 cm3, such as 0.5 cm3, such as 0.4 cm3, such as 0.3 cm3.

Nicotine tablets having a volume below the maximum stated volume may provide the user with desired disintegration time and dissolution time.

In an embodiment of the invention, the nicotine tablet comprises a third module.

In an embodiment of the invention, the third module is a surrounding coating layer.

The nicotine tablet may advantageously comprise an outer coating. The outer coating may protect the modular tablet from physical degradation, such as separation of the modules, or prevent moist attraction. Furthermore, an outer coating might protect the ingredients from chemical degradation.

In an embodiment of the invention, the third module being a surrounding coating layer is selected from the group consisting of hard coating, soft coating and edible film-coating or any combination thereof.

In an embodiment of the invention, the third module is free of nicotine.

In an advantageous embodiment of the invention, in the nicotine tablet consist of the first compressed module and the second compressed module.

In an embodiment of the invention, the nicotine tablet does not comprise a coating.

In an advantageous embodiment of the invention, the nicotine tablet does not comprise a coating.

In an advantageous embodiment of the invention, the first compressed module is fully disintegrated within 60 seconds, such as 45 seconds, such as 30 seconds upon oral administration.

The disintegration time of the first compressed module may be measured as described in example 3A.

In an advantageous embodiment of the invention, the nicotine tablet is fully disintegrated after no more than 15 minutes, such as no more than 10 minutes upon oral administration.

The disintegration time of the nicotine tablet may be measured as described in example 3B.

In an advantageous embodiment of the invention, the nicotine tablet is a non-tobacco tablet.

In an embodiment of the invention, the nicotine tablet is free of tobacco.

In an embodiment of the invention, the first module comprises sugar alcohol selected from the list consisting of xylitol, maltitol, mannitol, erythritol, isomalt, sorbitol, lactitol or any combination thereof, and the second module comprises sugar alcohol selected from the list consisting of xylitol, maltitol, mannitol, erythritol, isomalt, sorbitol, lactitol or any combination thereof.

In an embodiment of the invention, the first module comprises sugar alcohol in an amount of at least 50% by weight of the first compressed module, such as at least 60% by weight of the first compressed module, such as at least 70% by weight of the first compressed module, such as at least 80% by weight of the first compressed module, such as at least 85% by weight of the first compressed module, the sugar alcohol of the first module being selected from the list consisting of xylitol, maltitol, mannitol, erythritol, isomalt, sorbitol, lactitol or any combination thereof, the second compressed module comprises sugar alcohol in an amount of at least 50% by weight of the second compressed module, such as at least 60% by weight of the second compressed module, such as at least 70% by weight of the second compressed module, such as at least 80% by weight of the second compressed module, such as at least 85% by weight of the second compressed module, such as at least 90% by weight of the second compressed module the sugar alcohol of the second module being selected from the list consisting of xylitol, maltitol, mannitol, erythritol, isomalt, sorbitol, lactitol or any combination thereof.

In an embodiment of the invention, the alkaline pH regulating agent is selected from the group consisting of sodium carbonate, sodium bicarbonate, potassium carbonate, potassium bicarbonate, trometamol, amino acids, disodium hydrogen phosphate, dipotassium hydrogen phosphate, trisodium phosphate, tripotassium phosphate, or any combination thereof;

the acidic pH regulating agent is selected from the list consisting of phosphoric acid, mono-alkali dihydrogen phosphate, mono-alkali dihydrogen phosphate—di-alkali hydrogen phosphate mixture, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the sugar alcohol of the first module being selected from the list consisting of xylitol, maltitol, mannitol, erythritol, isomalt, sorbitol, lactitol or any combination thereof, the sugar alcohol of the second module being selected from the list consisting of xylitol, maltitol, mannitol, erythritol, isomalt, sorbitol, lactitol or any combination thereof, the alkaline pH regulating agent is selected from the group consisting of sodium carbonate, sodium bicarbonate, potassium carbonate, potassium bicarbonate, trometamol, amino acids, disodium hydrogen phosphate, dipotassium hydrogen phosphate, trisodium phosphate, tripotassium phosphate, or any combination thereof;

the acidic pH regulating agent is selected from the list consisting of phosphoric acid, mono-alkali dihydrogen phosphate, mono-alkali dihydrogen phosphate—di-alkali hydrogen phosphate mixture, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the first module comprises sugar alcohol in an amount of at least 50% by weight of the first compressed module, such as at least 60% by weight of the first compressed module, such as at least 70% by weight of the first compressed module, such as at least 80% by weight of the first compressed module, such as at least 85% by weight of the first compressed module, the sugar alcohol of the first module being selected from the list consisting of xylitol, maltitol, mannitol, erythritol, isomalt, sorbitol, lactitol or any combination thereof, the second compressed module comprises sugar alcohol in an amount of at least 50% by weight of the second compressed module, such as at least 60% by weight of the second compressed module, such as at least 70% by weight of the second compressed module, such as at least 80% by weight of the second compressed module, such as at least 85% by weight of the second compressed module, such as at least 90% by weight of the second compressed module, the sugar alcohol of the second module being selected from the list consisting of xylitol, maltitol, mannitol, erythritol, isomalt, sorbitol, lactitol or any combination thereof, the alkaline pH regulating agent is selected from the group consisting of sodium carbonate, sodium bicarbonate, potassium carbonate, potassium bicarbonate, trometamol, amino acids, disodium hydrogen phosphate, dipotassium hydrogen phosphate, trisodium phosphate, tripotassium phosphate, or any combination thereof;

the acidic pH regulating agent is selected from the list consisting of phosphoric acid, mono-alkali dihydrogen phosphate, mono-alkali dihydrogen phosphate—di-alkali hydrogen phosphate mixture, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

In an embodiment of the invention, the first compressed module comprises disintegrant in an amount of at least 0.5% by weight of the first compressed module, such as at least 1% by weight of the first compressed module, such as at least 2% by weight of the first compressed module, such as at least 3% by weight of the first compressed module, such as at least 4% by weight of the first compressed module, such as at least 5% by weight of the first compressed module, the disintegrant is selected from the list consisting of starch, pregelatinated starch, cellulose, modified cellulose, microcrystalline cellulose, alginates, ion-exchange resin, calcium silicate, crosslinked cellulose, crosslinked polyvinyl pyrrolidone, crosslinked starch, crosslinked alginic acid, and combinations thereof.

In an embodiment of the invention, the first compressed module comprises disintegrant in an amount of at least 0.5% by weight of the first compressed module, such as at least 1% by weight of the first compressed module, such as at least 2% by weight of the first compressed module, such as at least 3% by weight of the first compressed module, such as at least 4% by weight of the first compressed module, such as at least 5% by weight of the first compressed module, the disintegrant is selected from the list consisting of starch, pregelatinated starch, cellulose, modified cellulose, microcrystalline cellulose, alginates, ion-exchange resin, calcium silicate, crosslinked cellulose, crosslinked polyvinyl pyrrolidone, crosslinked starch, crosslinked alginic acid, and combinations thereof, sugar alcohol of the tablet being selected from the list consisting of xylitol, maltitol, mannitol, erythritol, isomalt, sorbitol, lactitol or any combination thereof.

In an embodiment of the invention, the first compressed module comprises disintegrant in an amount of at least 0.5% by weight of the first compressed module, such as at least 1% by weight of the first compressed module, such as at least 2% by weight of the first compressed module, such as at least 3% by weight of the first compressed module, such as at least 4% by weight of the first compressed module, such as at least 5% by weight of the first compressed module, the disintegrant is selected from the list consisting of starch, pregelatinated starch, cellulose, modified cellulose, microcrystalline cellulose, alginates, ion-exchange resin, calcium silicate, crosslinked cellulose, crosslinked polyvinyl pyrrolidone, crosslinked starch, crosslinked alginic acid, and combinations thereof, the tablet comprising sugar alcohol in an amount of at least 50% by weight of the tablet, such as at least 60% by weight of the se tablet, such as at least 70% by weight of the tablet, such as at least 80% by weight of the tablet, such as at least 85% by weight of the tablet, such as at least 90% by weight of the tablet, the sugar alcohol being selected from the list consisting of xylitol, maltitol, mannitol, erythritol, isomalt, sorbitol, lactitol or any combination thereof.

The invention further relates to a method of manufacturing a nicotine tablet according to the invention or any of its embodiments, the method comprising the steps of providing a first powdered composition and a second powdered composition, the first powdered composition comprising nicotine, disintegrant, and alkaline pH regulating agent, the second powdered composition comprising acidic pH regulating agent, pressing the second powdered composition and the first powdered composition to obtain the nicotine tablet comprising modules fused by compression.

In an advantageous embodiment of the invention, the method comprises the steps of pressing the second powdered composition to obtain a second module, and pressing the second module and the first powdered composition to obtain a first module fused by compression to the second module.

In an advantageous embodiment of the invention, the method comprises pressing the first powdered composition to obtain a first module, and pressing the first module and the second powdered composition to obtain a second module fused by compression to the first module.

In an advantageous embodiment of the invention, the method comprises the steps of pressing the second powdered composition to obtain a second module, and pressing the first powdered composition to obtain a first module fused by compression to the second module, wherein the first module surrounds the second module.

In an advantageous embodiment of the invention, the pressing is performed with a pressing force of at least 5 kN, such as at least 10 kN, such as at least 15 kN, such as at least 20 kN.

In an embodiment of the invention, the water-dissolvable nicotine tablet of the invention or any of its embodiments is obtained by the method of the invention or any of its embodiments.

The invention further relates to a water-dissolvable nicotine tablet comprising at least a first compressed module and a second compressed module, the first compressed module being a fast disintegrating module comprising nicotine and the compressed second module being a lozenge-module comprising acidic pH regulating agent.

In an embodiment of the invention, the water-dissolvable compressed nicotine tablet according to the embodiment above is made in accordance with the water-dissolvable compressed nicotine tablet first described or any of its embodiments, or obtained by the method of the invention or any of its embodiments.

The invention further relates to a water-dissolvable nicotine tablet comprising at least a first compressed module and a second compressed module, wherein the first compressed module comprises
nicotine,
alkaline pH regulating agent, and
disintegrant in an amount of at least 5% by weight of the first compressed module, and, wherein the second compressed module comprises
acidic pH regulating agent.

In an embodiment of the invention, the water-dissolvable compressed nicotine tablet according to the embodiment above is made in accordance with the water-dissolvable compressed nicotine tablet first described or any of its embodiments, or obtained by the method of the invention or any of its embodiments.

The invention further relates to a water-dissolvable nicotine tablet comprising at least a first compressed module and a second compressed module,
wherein the first compressed module is a FDT-layer and comprises
nicotine,
alkaline pH regulating agent, and
disintegrant, and,
wherein the second compressed module comprises
acidic pH regulating agent.

In an embodiment of the invention, the water-dissolvable compressed nicotine tablet according to the embodiment above is made in accordance with the water-dissolvable compressed nicotine tablet first described or any of its embodiments, or obtained by the method of the invention or any of its embodiments.

The invention further relates to a water- dissolvable nicotine tablet comprising at least a first compressed module and a second compressed module,
wherein the first compressed module comprises
nicotine,
alkaline pH regulating agent, and
disintegrant, and,
wherein the second compressed module comprises
acidic pH regulating agent.
Wherein the first compressed module has a shorter dissolution time than the dissolution time of the second compressed module.

In an embodiment of the invention, the water-dissolvable compressed nicotine tablet according to the embodiment above is made in accordance with the water-dissolvable compressed nicotine tablet first described or any of its embodiments, or obtained by the method of the invention or any of its embodiments.

The invention further relates to a water-dissolvable nicotine tablet comprising at least a first compressed module and a second compressed module,
wherein the first compressed module comprises
nicotine,
alkaline pH regulating agent, and
disintegrant, and,
wherein the second compressed module comprises
acidic pH regulating agent.
Wherein the difference in disintegration time between the first and the second compressed module is at least 2 minutes.

In an embodiment of the invention, the water-dissolvable compressed nicotine tablet according to the embodiment above is made in accordance with the water-dissolvable compressed nicotine tablet first described or any of its embodiments, or obtained by the method of the invention or any of its embodiments.

DETAILED DESCRIPTION

As used herein the term "water-dissolvable nicotine tablet" refers to a compressed tablet that overall is dissolvable in water. While the nicotine lozenge of the invention comprises dissolvable FDT module, it also comprises dissolvable lozenge module. Thus, the nicotine tablet of course does not comprise e.g. chewing gum modules that does not dissolve in water. Furthermore, the nicotine tablet is water-dissolvable in the sense that it disintegrates and that main constituents dissolve in water. The nicotine tablet of the invention is a compressed tablet, formed by compression of at least a first powdered composition and a second powdered composition to give the first and second compressed modules, respectively.

The water-dissolvable nicotine tablet may comprise some amounts of water-insoluble material, such as no more than 10% by weight of the tablet of e.g. MCC. Thus, the majority of the water-dissolvable nicotine tablet is comprised of water-soluble material, such as more than 90% by weight of the tablet.

The nicotine tablet may disintegrate and dissolve within a period of at least 2 minutes upon oral administration, such as at least 3 minutes, such as at least 4 minutes, such as at least 5 minutes.

As used herein, the term "FDT-module" (Fast Disintegrating Tablet-module) refers a module having the characteristics of a so-called fast disintegrating tablet. Fast disintegrating tablets, also sometimes referred to as orally disintegrating tablets (ODT), generally exhibits rapid oral disintegration with no need for chewing or drinking liquids to ingest these products.

FDT-modules of the invention exhibits fast disintegration, typically below 60 seconds from placing it in the mouth, or even faster such as 30 seconds from placing it in the mouth. In some embodiments of the invention, the FDT-modules disintegrates within 30 seconds, such as within 20 seconds, such as within 15 seconds.

As used herein the term "lozenge-module" refers to a module imparting lozenge properties, i.e. a module that dissolve or disintegrate over minutes in the mouth, whereby its constituents are released, e.g. acidic pH regulating agents, flavor, etc. depending on the specific embodiment. For example, the lozenge-module may disintegrate and dissolve within a period of at least 2 minutes upon oral administration, such as at least 3 minutes, such as at least 4 minutes, such as at least 5 minutes.

As used herein, the term "disintegrate" refers to a reduction of an object to components, fragments or particles. Disintegration time may be measured in vitro or in vivo. Unless otherwise stated, the in vitro measurements are carried out in accordance with European Pharmacopeia 9.0, section 2.9.1, Disintegration of tablets and capsules. In vivo measurements are carried out as described in example 3B.

As used herein, the term "dissolve" is the process where a solid substance enters a solvent (oral saliva) to yield a solution. Unless otherwise stated, dissolving implies a full dissolving of the compound in question.

As used herein, the term "disintegrant" refers to an ingredient facilitating disintegration of an FDT-module, when the FDT-module comes into contact with saliva. Disintegrants may often be considered as measure promoting the break-up of the module into smaller fragments upon administration to facilitate nicotine release and eventual absorption.

As used herein, the term "binder" refers to an ingredient promoting cohesiveness to the powder composition during tablet production and thereby facilitating production of modules and thereby nicotine tablets with a desirable mechanical strength.

In preferred embodiments of the invention, the second compressed module comprises binder.

As used herein, the term "nicotine" refers to nicotine in any form, including free base nicotine; nicotine salts; nicotine bound to a carrier, such as nicotine bound to ion exchange resins, nicotine bound to zeolites; nicotine bound to fibres or microspheres, nicotine bound to CaCO3, nicotine bound to sugar alcohol; and mixtures thereof. Bound is here to be understood as nicotine being ionically bound, adsorbed or absorbed onto the carrier, depending on the type of carrier.

When referring to nicotine amounts in milligram, the amounts are to be understood as the nicotine dose, i.e. the amounts refers to the amount of pure nicotine.

When referring to nicotine amounts in weight percent, the amount are to be understood as the actual amount of the nicotine source in relation to the specified term, such as the first compressed module or the nicotine tablet. I.e. a first compressed module of 75 mg comprising nicotine bitartrate in an amount of 4% by weight of the first compressed module, refers to a first compressed module comprising 3 mg of nicotine bitartrate (i.e. 1 mg of pure nicotine).

Nicotine also covers nicotine not obtained from tobacco, often referred to as synthetic nicotine. Nicotine is included in the first compressed module. In embodiments nicotine is included in the first compressed module but not in the second compressed module.

As used herein the term "free-base nicotine" refers to non-protonated form of nicotine. Free-base nicotine may be provided as a liquid or as mixed with an amount of ion exchange resin; water-soluble compositions, such as sugar alcohols or water-soluble fibers; or water-insoluble fibers; or modified calcium carbonate. While free-base nicotine includes both free-base nicotine extracted from tobacco as well as synthetically manufactured free-base nicotine, the free-base nicotine is not provided in the form of tobacco or powdered tobacco.

As used herein, the term "nicotine salt" refers to nicotine in ionized form bound to a counterion.

As used herein, the term "NBT" refers to nicotine bitartrate and hydrates thereof.

As used herein, the term "%" and "percent" refers to percent by weight, unless otherwise is stated.

As used herein, the term "release of nicotine" refers to the nicotine being made bioavailable, i.e.

available for absorption over the mucous membrane in the oral cavity. While some forms of nicotine require dissolution for being bioavailable, other forms may be readily absorbed into the body without dissolution. For example, in order for the nicotine to be bioavailable, the matrix of the tablet should be disintegrated. Some forms of nicotine require the nicotine to further be released from e.g. a carrier, e.g. nicotine from a nicotine-ion exchange resin such as nicotine polacrilex. Other nicotine forms, such nicotine salts, hereunder nicotine bitartrate, may readily dissolve upon disintegration of the matrix of the tablet. Still, some nicotine forms may not require dissolving. This applies for e.g. nicotine free base, which is released upon disintegration of the solid formulation matrix.

As used herein, the term "pH regulating agent" refers to agents, which active adjust and regulates the pH value of the solution to which they have been added or are to be added. Thus, pH regulating agents may be acidic or alkaline.

An acidic pH regulating agent, when added to water having a pH of 7.0 at a temperature of 25 degrees Celsius will induce a pH below 7.5, whereas an alkaline pH regulating agent, when added to water having a pH of 7.0 will induce a pH above 7.5.

When more than one pH regulating agents are included in the same module, these form a combined pH regulating agent. The combined pH regulating agent is an acidic pH regulating agent when inducing a pH below 7.5 when added to water having a pH of 7.0 measured at a temperature of 25 degrees Celsius, atmospheric pressure, or an alkaline pH regulating agent when inducing a pH above 7.5 when added to water having a pH of 7.0 measured at a temperature of 25 degrees Celsius, atmospheric pressure.

In other words, an acidic pH regulating agent can in some embodiments e.g. be an acidic buffering system comprising a combination of pH regulating agents, as long as the buffering system induces a pH below 7.5 when added to water having a pH of 7.0 measured at a temperature of 25 degrees Celsius, atmospheric pressure.

On the other hand, pH regulating agents does not including substances and compositions that can only affect the pH by dilution. Furthermore, pH regulating agents does not include e.g. flavors, fillers, etc.

In some preferred embodiments, the acidic pH regulating agent, when added to water having a pH of 7.0 will induce a pH below 7.0 when measured at 25 degrees Celsius and atmospheric pressure.

As used herein, a "molar ratio" refers to the ratio of the molar content of the first component divided by the molar content of the second component.

The relative content between the first component and the second component may also be presented as equivalents of the first component relative to the second component.

Thus, a second compressed module comprising acidic pH regulating agent in a molar ratio of 1.0 relative to the amount of nicotine in the first compressed module, may also be presented as a nicotine tablet comprising 1.0 eq. of acidic pH regulating agent relative to the amount of nicotine in the first compressed module, i.e. a nicotine tablet comprising 1.0 eq. of acidic pH regulating agent and 1.0 eq. of nicotine in the first compressed module.

When referring to amounts of an ingredient by terms such as "less than", "no more than", this generally refers to the particular ingredient being absent or present in a range from trace amounts to the specified maximum amount.

As used herein the term "flavor" is understood as having its ordinary meaning within the art. Flavor includes liquid and powdered flavors. Thus, flavors do of course not include sweeteners (such as sugar, sugar alcohols and high intensity sweeteners), or acids providing pure acidity/sourness, nor compounds providing pure saltiness (e.g. NaCl) or pure bitterness. The flavors can be natural or synthetic flavors.

Typically, the nicotine tablet may comprises of ingredients selected from the group consisting of fillers, flavors, binders, disintegrants, hereunder super disintegrants, emulsifiers, antioxidants, pH regulating agents hereunder alkaline and acidic pH regulating agents, high intensity sweeteners, colors, glidants, lubricants, or any combination thereof.

In an advantageous embodiment of the invention, the tablet comprises bulk sweetener as filler ingredient.

In an advantageous embodiment of the invention, the first compressed module comprises bulk sweetener as filler ingredient.

In an advantageous embodiment of the invention, the second compressed module comprises bulk sweetener as filler ingredient.

In an advantageous embodiment of the invention, the first and second compressed module comprise bulk sweetener as filler ingredient.

In embodiments where the nicotine tablet comprises bulk sweeteners, different bulk sweeteners may be used. Bulk sweeteners include sugar sweetener and/or sugarless sweetener.

Sugar sweeteners generally include, but are not limited to saccharide-containing components, such as sucrose, dextrose, maltose, saccharose, lactose, sorbose, dextrin, trehalose, D-tagatose, dried invert sugar, fructose, levulose, galactose, and the like, alone or in combination.

Sugarless sweeteners generally include, but are not limited to sugar alcohols (also sometimes referred to as polyols) such as xylitol, maltitol, mannitol, erythritol, isomalt, sorbitol and lactitol.

Combinations of sugar and/or non-sugar sweeteners may be used in the nicotine tablet.

The bulk sweeteners may often support the flavor profile of the nicotine tablet.

In embodiment of the invention, bulk sweeteners may be supplemented with other usable fillers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, fibers, plant fibers, such as wheat fiber, oat fiber, pea fiber, and combinations thereof.

High intensity artificial sweetening agents can also be used in combination with the above bulk sweeteners. For example, high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (such as from about 0.02 to about 8% by weight).

In embodiments where the nicotine tablet comprises flavor, different flavors may be used.

Usable flavors including as examples almond, almond amaretto, apple, Bavarian cream, black cherry, black sesame seed, blueberry, brown sugar, bubblegum, butterscotch, cappuccino, caramel, caramel cappuccino, cheesecake (graham crust), cinnamon redhots, cotton candy, circus cotton candy, clove, coconut, coffee, clear coffee, double chocolate, energy cow, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry, kiwi, tropical punch, tutti frutti, vanilla, or any combination thereof.

According to an embodiment of the invention, flavor may be used as taste masking for the nicotine and/or taste masking of the alkaline pH regulating agent.

In an embodiment of the invention the nicotine tablet comprises glidant. Silicon dioxide may be used as a glidant. Other glidants usable for the tablet may also be used within the scope of the invention.

In an embodiment of the invention the nicotine tablet comprises lubricant. Magnesium stearate and/or sodium stearyl fumarate may be used as a lubricant. Other lubricants usable for the tablet may also be used within the scope of the invention.

Ready to use systems may be used within the scope of the invention. Typically, such ready-to-use systems may e.g. replace filler, disintegrant, glidant or similar with a single powder mix. Suitable ready-to-use systems for the purpose, but not limited to, include Pearlitol Flash (Roquette), Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma). Using a ready to use systems comprising a disintegrant may be especially advantageous.

In order to obtain an FDT-module being designed for disintegrating within a period of 60 second upon oral administration, a range of parameters can be adjusted.

First, by varying the composition, the disintegration time can be altered. Using ingredients with a high water-solubility may facilitate a lowered disintegration time.

Particularly, including a disintegrant may significantly influence the disintegration time, subject to the total composition of the first compressed module. Also, by varying the amount and type of the disintegrant, the disintegration time may be further adjusted. For example, if the first compressed module having a lower disintegration time is desired, the percentage content of disintegrant may be increased and/or the type of disintegrant may be at least partly exchanged for a more effective disintegrant, such as a super disintegrant.

It is noted, that some ingredients have a dual function, such as some ingredients may be used as disintegrants in one contexts and as binders in another context. For example, some disintegrants may have binding properties or visa versa. Hence, the list of binders may have overlap with the list of disintegrants.

In some embodiments, the disintegrant may comprise a combination of regular disintegrant and super-disintegrant, where the regular disintegrant may contribute with some disintegrating properties upon oral administration and desirable binding properties during production, and the super disintegrant ensures a fast disintegration upon oral administration.

Also, decreasing the particle size of the disintegrant tends to lower the disintegration time, likely due to an increased surface area to volume ratio.

Furthermore, the compression force used to press the first compressed module correlate significantly with the obtained hardness of the first compressed module, such that a high compression force typically increases the hardness of the obtained first compressed module. By adjusting the hardness of a first compressed module, the disintegration time may also be influenced, such that a lowered hardness typically gives a shorter disintegration time. Here it has been observed for a number of compositions that by applying the correct compression force a disintegration time below 60 seconds upon oral administration can be achieved, whereas a too high compression force may result in a longer disintegration time above 60 seconds. In this regard it is noted that the threshold compression force may vary significantly, depending on other parameters, such as overall composition, content and type of disintegrant, etc. When, for example, a certain setup results in a too slow disintegration, a further way of adjusting may be to replace a regular disintegrant with a super disintegrant, i.e. which facilitates disintegration in a more efficient way.

Increasing the water-solubility may also be facilitated by exchanging ingredients with low water-solubility with ingredients having higher water-solubility. For example, using sugar alcohols as fillers may be very advantageous insofar that the sugar alcohols have a higher water solubility than alternative fillers.

Moreover, using sugar alcohols with a lower compact ability leads to lower disintegration time. Too low compact ability may compromise the mechanical strength of the first compressed module and the second compressed module and lead to undesirably high friability and risk of cracks etc.

Another examples of parameters that may be adjusted in order to obtain a first compressed module being designed for disintegrating within a period of 60 second upon oral administration include the overall design of the tablet. In some embodiments, such as a tablet comprising a second compressed module being a core and a first compressed module being a surrounding compressed coating, the first compressed module will have a higher exposed surface area compared to a layered tablet design. Increased exposed surface area may decrease disintegration time.

Further examples of parameters that may be adjusted in order to obtain a first compressed module being designed for disintegrating within a period of 60 second upon oral administration include size and shape of the first compressed module and overall tablet. The larger volume of the first compressed module, the longer the disintegration time and thus release time of the nicotine and alkaline pH regulating agent.

For example, increasing the flatness of a layered tablet (e.g. quantified by a diameter to height ratio) for e.g. a disc-shaped tablet typically decreases disintegration time by increasing the surface-to-volume. As long as the tablet has a satisfactory mechanical strength, flatness may be increased.

Also, modifying the cross-sectional profile from a convex type nicotine tablet to a concave shaped tablet lowers the disintegration time. It is noted that this may to some degree lower the mechanical strength of the tablet, however, as long as it is satisfactory, pursuing the concave cross-section may help to increase disintegration and thus lower the disintegration time.

Further, the type and amount of lubricant, if any, may be adjusted to optimize disintegration time.

For example, using Sodium stearyl fumarate (SSF) typically leads to a lower disintegration time compared to when using magnesium stearate MgSt.

Thus, a wide range of parameters may be adjusted when designing the first compressed module with a disintegration time of 60 second upon oral administration.

The same parameter may be adjusted when designing the second compressed module to have a disintegration time of at least 2 minutes upon oral administration, such as at least 3 minutes, such as at least 4 minutes, such as at least 5 minutes.

The disintegration time of the second compressed module equals the disintegration time of the nicotine tablet, since the first compressed module is designed to disintegrate within 60 seconds from oral administration.

In an embodiment of the invention the second compressed module of the nicotine tablet comprises binders.

It is noted, that some ingredients have a dual function such as some ingredients may be used as disintegrants in one contexts and as binders in another context. For example, some disintegrants may have binding properties or visa versa. Hence, the list of binders may have overlap with the list of disintegrants.

In an advantageous embodiment of the invention, the second compressed module comprises a binder.

Usable binders include any of, but are not limited to polysaccharides and modified polysaccharides, such as acacia gum, agar, carrageenan, chitosan, inulin, xanthan gum, tragacanth, pullulan, guar gum, pectin, chitin; alginic acid or a salt thereof; carbomer; cellulose; copovidone; gelatin; polycarbophil or a salt thereof; microcrystalline cellulose; polyvinyl alcohol;; starch; pregelatinated starch; modified cellulose such as carboxymethylcellulose, ethylcellulose, hydroxyethyl cellulose, hydroxyethyl methylcellulose, hydroxypropyl cellulose, methylcellulose, hydroxypropylmethyl cellulose; polyethylene glycol; polyethylene oxide; , and mixtures thereof In one embodiment, the binder included within the second compressed module of the tablets of the present invention may be selected from the group consisting of alginic acid or a salt thereof, polycarbophil or a salt thereof, xanthan gum, microcrystalline cellulose, hydroxypropylmethyl cellulose (HPMC), hydroxypropyl cellulose (HPC), and mixtures thereof.

In one embodiment, the binder included within the second compressed module of the tablets of the present invention may be selected from the group consisting of alginic acid or a salt thereof, polycarbophil or a salt thereof, xanthan gum, and mixtures thereof.

In one embodiment, the binder included within the second compressed module of the tablets of the present invention may be selected from the group consisting of microcrystalline cellulose, hydroxypropylmethyl cellulose, hydroxypropyl cellulose, or a mixture thereof.

In some embodiments, the first compressed module comprises binder.

Also, when using binders, e.g. to obtain a higher cohesiveness and mechanical strength of a compressed module, the amount of such binders may be adjusted as to obtain a higher or lower disintegration rate and thus a longer or shorter disintegration time.

In some embodiments, the first compressed module comprises binder and super-disintegrant.

Binder may advantageously be included in the first compressed module, whereby a desirable cohesiveness during tableting is achieved. By also including super-disintegrant in the module, a desirable low disintegration time of the module may be obtained.

EXAMPLES

Example 1A: Preparation of Tablets Comprising a Second Module being a Tablet Core Fully Surrounded by a First Module The composition of second module is prepared by pouring about half of the filler into a mixing bowl, followed by the remaining ingredients except lubricant, and finally the remaining filler. The ingredients are tumbled/mixed with a mixer (Turbula or Duma) for 4-10 min at 49 rpm.

Lubricant is added and the ingredients are further mixed for 1-2 min at 49 rpm.

The composition of first module is prepared by pouring all the ingredients except lubricant, into a mixing bowl. The ingredients are tumbled/mixed with a mixer (Turbula or Duma) for 4-10 min at 49 rpm.

Lubricant is added and the ingredients are further mixed for 1-2 min at 49 rpm.

The lubricated powder blends are sequentially transferred to the hopper of a tableting machine.

The composition of the second module is compressed at a compression force of approximately 3 kN to form the tablet core.

The tablet core, i.e. the compressed second module, is transferred to a second compression device, whereafter the composition of the first module is press coated around the core.

The composition is compressed at a compression force of about 15-20 kN to form a first compressed module surrounding the second module.

The fast disintegrating tablets are manufactured on a rotary press machine, for example Manestry DryCota tablet press. The tablet machine is commissioned by adjusting the fill depth and compression force so the weight and hardness of nicotine tablets match the acceptance criteria.

Example 1B: Preparation of Tablets Comprising a Second Module Being a Tablet Core Partly Surrounded by a First Module.

The composition of second module is prepared by pouring about half of the filler into a mixing bowl, followed by the remaining ingredients except lubricant, and finally the remaining filler. The ingredients are tumbled/mixed with a mixer (Turbula or Duma) for 4-10 min at 49 rpm.

Lubricant is added and the ingredients are further mixed for 1-2 min at 49 rpm.

The composition of first module is prepared by pouring all the ingredients except lubricant, into a mixing bowl. The ingredients are tumbled/mixed with a mixer (Turbula or Duma) for 4-10 min at 49 rpm.

Lubricant is added and the ingredients are further mixed for 1-2 min at 49 rpm.

The lubricated powder blends are sequentially transferred to the hopper of a tableting machine.

The composition of the second module is compressed at a compression force of approximately 3 kN to form second modules.

The composition of the first module is transferred to the tableting machine, the second module is placed in the punch cylinder, and the first composition is compressed and fused by compression to the second module at a compression force of about 15-20 kN to form a first compressed module partially surrounding the second module.

The tablet machine is commissioned by adjusting the fill depth and compression force so the weight and hardness of nicotine tablets match the acceptance criteria.

Example 1C

Preparation of tablets comprising a first and a second module being tablet layers.

The composition of second module is prepared by pouring about half of the filler into a mixing bowl, followed by the remaining ingredients except lubricant, and finally the remaining filler. The ingredients are tumbled/mixed with a mixer (Turbula or Duma) for 4-10 min at 49 rpm.

Lubricant is added and the ingredients are further mixed for 1-2 min at 49 rpm.

The composition of first module is prepared by pouring all the ingredients except lubricant, into a mixing bowl. The ingredients are tumbled/mixed with a mixer (Turbula or Duma) for 4-10 min at 49 rpm.

Lubricant is added and the ingredients are further mixed for 1-2 min at 49 rpm.

The lubricated powder blends are sequentially transferred to the hopper of a tableting machine.

The second module is then compressed at a compression force of about 3-6 kN, after which the first module is fused by compression to the second module at a compression force of about 15-20 kN. Punch used unless otherwise specified: 10.00 mm, circular, shallow concave, D tooling.

The fast disintegrating tablets are manufactured on a lab scale machine, for example RIVA Piccola tablet press. The tablet machine is commissioned by adjusting the fill depth and compression force so the weight and hardness of tablets match the acceptance criteria. A pre-compression force could be included to avoid capping.

Example 2: Tablet Compositions

Example 2A 450 mg nicotine tablets were made each with 350 mg second module and 100 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 1

Compositions of first and second compressed modules.

| | NT1 | NT2 | NT3 | NT4 | NT5 | NT6 | NT7 | NT8 | C1 |
|---|---|---|---|---|---|---|---|---|---|
| Nicotine dose (mg) | 0.5 | 1.0 | 1.5 | 2.0 | 2.5 | 3.0 | 4.0 | 5.0 | 1.0 |
| Acidic pH regulating agent [eq]* | 3.5 | 3.5 | 3.5 | 3.5 | 3.5 | 3.5 | 3.5 | 3.5 | 0 |
| Raw material 1$^{st}$ module | | | Content in weight percent of 1$^{st}$ module | | | | | | |
| Mannitol | 78.0 | 76.5 | 75.0 | 73.5 | 72.0 | 70.5 | 67.5 | 64.5 | 76.5 |
| Disintegrant | 15 | 15 | 15 | 15 | 15 | 15 | 15 | 15 | 15 |

TABLE 1-continued

Compositions of first and second compressed modules.

|  | NT1 | NT2 | NT3 | NT4 | NT5 | NT6 | NT7 | NT8 | C1 |
|---|---|---|---|---|---|---|---|---|---|
| Sodium carbonate | 5 | 5 | 5 | 5 | 5 | 5 | 5 | 5 | 5 |
| NBT | 1.5 | 3.0 | 4.5 | 6.0 | 7.5 | 9 | 12.0 | 15.0 | 3.0 |
| MgSt | 0.5 | 0.5 | 0.5 | 0.5 | 0.5 | 0.5 | 0.5 | 0.5 | 0.5 |
| Total 1$^{st}$ module | 100 | 100 | 100 | 100 | 100 | 100 | 100 | 100 | 100 |
| Raw material 2$^{nd}$ module | \multicolumn{9}{l}{Content in weight percent of 2$^{nd}$ module} |
| Mannitol | 97.65 | 97.05 | 96.45 | 95.85 | 95.25 | 94.65 | 93.45 | 92.25 | 98.25 |
| Citric acid | 0.6 | 1.2 | 1.8 | 2.4 | 3.0 | 3.6 | 4.8 | 6.0 | — |
| Flavor | 1 | 1 | 1 | 1 | 1 | 1 | 1 | 1 | 1 |
| HIS | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 |
| Total 2$^{nd}$ module | 100 | 100 | 100 | 100 | 100 | 100 | 100 | 100 | 100 |

NBT = Nicotine bi-tartrate (nicotine content of 32.38% by weight).

HIS = high intensity sweetener.

*The amount of acidic pH regulating agent in the second module is presented as equivalents relative to the nicotine in the first module.

Mannitol may be used as the sugar alcohol in first module and second module. Other usable sugar alcohols for use in second module may include xylitol, maltitol, erythritol, isomalt, sorbitol, lactitol or any combination thereof. Of these erythritol, isomalt, sorbitol, xylitol, or any combination thereof are particularly preferred. Other usable sugar alcohols for use in first module may include xylitol, maltitol, mannitol, erythritol, isomalt, sorbitol, lactitol or any combination thereof. Of these xylitol, erythritol, isomalt, or any combination thereof, are particularly preferred.

The disintegrant in the amount in first module may e.g. be a starch disintegrant. Examples of other usable disintegrates include pregelatinated starch, cellulose, modified cellulose, microcrystalline cellulose, alginates, ion-exchange resin, calcium silicate, and combinations thereof. Alternatively, super-disintegrants such as crosslinked cellulose, crosslinked polyvinyl pyrrolidone, crosslinked starch, crosslinked alginic acid, and combinations thereof, could have been used, although the amount of super-disintegrant used might advantageously have been reduced.

Preferred high intensity sweeteners (HIS) may e.g. be sucralose, acesulfame potassium, and mixtures thereof. Other high intensity sweeteners, such as aspartame, salts of acesulfame, such as acesulfame potassium, alitame, saccharin and its salts, cyclamic acid and its salts, glycyrrhizin, dihydrochalcones, thaumatin, monellin, stevioside, alone or in combination, are also usable within the scope of the invention.

Fruit flavors, and mixtures thereof, menthol, peppermint, and mixtures thereof, may be used in the above formulations as flavors. Other flavors may also be used within the scope of the invention.

Sodium carbonate is used as the alkaline pH regulating agent in the first module. Further usable alkaline pH regulating agents include sodium bicarbonate, potassium carbonate, potassium bicarbonate, trometamol, amino acids, disodium hydrogen phosphate, dipotassium hydrogen phosphate, trisodium phosphate, tripotassium phosphate, or any combination thereof.

Citric acid is used as the acidic pH regulating agent in the second module. Further usable acidic pH regulating agents include phosphoric acid, monosodium dihydrogen phosphate, monopotassium dihydrogen phosphate, monosodium dihydrogen citrate, monopotassium dihydrogen citrate, disodium hydrogen citrate, dipotassium hydrogen citrate, malic acid, monosodium malate, monopotassium malate, succinic acid, monosodium succinate, monopotassium succinate, tartaric acid, monosodium tartrate, monopotassium tartrate, acetic acid, sorbic acid, benzoic acid, formic acid, and combinations thereof.

In the above MgSt (Magnesium stearate) is used as lubricant. Other lubricants, such as sodium stearyl fumerate may also be usable within the scope of the invention.

C1 is a comparative example not comprising acidic pH regulating agent in the second compressed module.

Examples 2B 450 mg nicotine tablets were made each with 350 mg second module and 100 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 2

Compositions of first and second modules.

|  | NT11 | NT12 | NT13 | NT14 | NT15 | NT16 | NT17 | NT18 | C2 |
|---|---|---|---|---|---|---|---|---|---|
| Nicotine dose (mg) | 1.0 | 1.0 | 1.0 | 1.0 | 1.0 | 1.0 | 1.0 | 1.0 | 1.0 |
| Acidic pH regulating agent [eq]* | 3.5 | 3.5 | 3.5 | 3.5 | 3.5 | 3.5 | 3.5 | 3.5 | 3.5 |
| Raw material $1^{st}$ module | Content in weight percent of $1^{st}$ module | | | | | | | | |
| Mannitol | 90.5 | 89.5 | 87.5 | 85.5 | 83.5 | 81.5 | 79.5 | 77.5 | 91.5 |
| Super-disintegrant | 1 | 2 | 4 | 6 | 8 | 10 | 12 | 14 | — |
| Sodium carbonate | 5 | 5 | 5 | 5 | 5 | 5 | 5 | 5 | 5 |
| NBT | 3.0 | 3.0 | 3.0 | 3.0 | 3.0 | 3.0 | 3.0 | 3.0 | 3.0 |
| MgSt | 0.5 | 0.5 | 0.5 | 0.5 | 0.5 | 0.5 | 0.5 | 0.5 | 0.5 |
| Total $1^{st}$ module | 100 | 100 | 100 | 100 | 100 | 100 | 100 | 100 | 100 |
| Raw material $2^{nd}$ module | Content in weight percent of $2^{nd}$ module | | | | | | | | |
| Mannitol | 97.05 | 97.05 | 97.05 | 97.05 | 97.05 | 97.05 | 97.05 | 97.05 | 97.05 |
| Citric acid | 1.2 | 1.2 | 1.2 | 1.2 | 1.2 | 1.2 | 1.2 | 1.2 | 1.2 |
| Flavor | 1 | 1 | 1 | 1 | 1 | 1 | 1 | 1 | 1 |
| HIS | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 |
| Total $2^{nd}$ module | 100 | 100 | 100 | 100 | 100 | 100 | 100 | 100 | 100 |

NBT = Nicotine bi-tartrate (nicotine content of 32.38% by weight).
HIS = high intensity sweetener.
*The amount of acidic pH regulating agent in the second module is presented as equivalents relative to the nicotine in the first module.

In NT11-NT18, Crosslinked polyvinyl pyrrolidone, here Crospovidone®, Kollidon CL-F is used as a super disintegrant. Alternative super disintegrants may e.g. include cross-linked cellulose (such as Croscarmellose®), crosslinked starch (such as sodium starch glycolate) and crosslinked alginic acid (such as Alginic acid NF®).

C2 is a comparative example not comprising disintegrant in the first compressed module.

Alternative ingredients as described in relation to NT1-NT8 may also be applied for NT11-NT18.

Example 2C 450 mg nicotine tablets were made each with 350 mg second module and 100 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 3

Compositions of first and second compressed modules.

|  | NT21 | NT22 | NT23 | NT24 | NT25 | NT26 | NT27 | NT28 | NT29 | NT30 |
|---|---|---|---|---|---|---|---|---|---|---|
| Nicotine dose (mg) | 1.0 | 1.0 | 1.0 | 1.0 | 1.0 | 1.0 | 1.0 | 1.0 | 1.0 | 1.0 |
| Acidic pH regulating agent [eq]* | 0.5 | 1.0 | 2.0 | 4.0 | 5.0 | 3.5 | 5.0 | 7.5 | 11.5 | 15.0 |
| Raw material $1^{st}$ module | Content in weight percent of $1^{st}$ module | | | | | | | | | |
| Mannitol | 86.5 | 86.5 | 86.5 | 86.5 | 86.5 | 86.5 | 86.5 | 86.5 | 86.5 | 86.5 |
| Super-disintegrant | 5 | 5 | 5 | 5 | 5 | 5 | 5 | 5 | 5 | 5 |
| Sodium carbonate | 5 | 5 | 5 | 5 | 5 | 5 | 5 | 5 | 5 | 5 |

TABLE 3-continued

Compositions of first and second compressed modules.

| | NT21 | NT22 | NT23 | NT24 | NT25 | NT26 | NT27 | NT28 | NT29 | NT30 |
|---|---|---|---|---|---|---|---|---|---|---|
| NBT | 3.0 | 3.0 | 3.0 | 3.0 | 3.0 | 3.0 | 3.0 | 3.0 | 3.0 | 3.0 |
| MgSt | 0.5 | 0.5 | 0.5 | 0.5 | 0.5 | 0.5 | 0.5 | 0.5 | 0.5 | 0.5 |
| Total 1$^{st}$ module | 100 | 100 | 100 | 100 | 100 | 100 | 100 | 100 | 100 | 100 |
| Raw material 2$^{nd}$ module | \multicolumn{10}{c}{Content in weight percent of 2$^{nd}$ module} |
| Mannitol | 98.23 | 97.91 | 97.57 | 96.90 | 96.55 | 97.47 | 97.13 | 96.56 | 95.67 | 93.15 |
| Citric acid | 0.02 | 0.34 | 0.68 | 1.35 | 1.70 | — | — | — | — | 5.1 |
| Monosodium dihydrogen phosphate | — | — | — | — | — | 0.53 | 0.74 | 1.06 | 1.70 | — |
| Disodium hydrogen phosphate | — | — | — | — | — | 0.25 | 0.38 | 0.63 | 0.88 | — |
| Flavor | 1 | 1 | 1 | 1 | 1 | 1 | 1 | 1 | 1 | 1 |
| HIS | 0.25 | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 | 0.5 |
| Total 2$^{nd}$ module | 100 | 100 | 100 | 100 | 100 | 100 | 100 | 100 | 100 | 100 |

NBT = Nicotine bi-tartrate (nicotine content of 32.38% by weight).
HIS = high intensity sweetener.
*The amount of acidic pH regulating agent(s) in the second module is presented as equivalents relative to the nicotine in the first module. Where the acidic pH regulating agent is mixture of pH regulating agents, the molar ratio refers to the total molar amount of acidic pH regulating agent(s) relative to the molar amount of nicotine in the first compressed module.
Super disintegrant is used in the first compressed module. The super-disintegrant used may e.g. be crosslinked polyvinyl pyrrolidone, such as Crosspovidone ®. Other usable super-disintegrants, such as crosslinked cellulose, crosslinked starch, crosslinked alginic acid, and combinations thereof could have been applied.

Sodium carbonate is used as the alkaline pH regulating agent in the first module. Further usable alkaline pH regulating agents include sodium bicarbonate, potassium carbonate, potassium bicarbonate, trometamol, amino acids, disodium hydrogen phosphate, dipotassium hydrogen phosphate, trisodium phosphate, tripotassium phosphate, or any combination thereof.

Citric acid is used as the acidic pH regulating agent in the second module of NT21-25 and NT30. Further usable acidic pH regulating agents include phosphoric acid, monosodium dihydrogen phosphate, monopotassium dihydrogen phosphate, monosodium dihydrogen citrate, monopotassium dihydrogen citrate, disodium hydrogen citrate, dipotassium hydrogen citrate, malic acid, monosodium malate, monopotassium malate, succinic acid, monosodium succinate, monopotassium succinate, tartaric acid, monosodium tartrate, monopotassium tartrate, acetic acid, sorbic acid, benzoic acid, formic acid, and combinations thereof.

Monosodium dihydrogen phosphate-disodium hydrogen phosphate mixture is used as the acidic pH regulating system in the second module of NT26-29. Further usable acidic pH regulating agents include phosphoric acid, monosodium dihydrogen phosphate, monopotassium dihydrogen phosphate, citric acid, monosodium dihydrogen citrate, monopotassium dihydrogen citrate, disodium hydrogen citrate, dipotassium hydrogen citrate, malic acid, monosodium malate, monopotassium malate, succinic acid, monosodium succinate, monopotassium succinate, tartaric acid, monosodium tartrate, monopotassium tartrate, acetic acid, sorbic acid, benzoic acid, formic acid, and combinations thereof.

Alternative ingredients as described in relation to NT1-NT8 may also be applied for NT21-NT30.

Example 2D—Varying Acidic pH Regulating Agent and Equivalents Used 300 mg nicotine tablets were made each with 225 mg second module and 75 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 4

Compositions of first and second modules.

| | NT31 | NT32 | NT33 | NT34 | NT35 | NT36 | NT37 | NT38 | NT39 |
|---|---|---|---|---|---|---|---|---|---|
| Nicotine dose (mg) | 1.0 | 1.0 | 1.0 | 1.0 | 1.0 | 1.0 | 1.0 | 1.0 | 1.0 |
| Acidic pH regulating agent [eq]* | 2.0 | 2.0 | 2.0 | 2.0 | 2.0 | 2.0 | 1.0 | 3.0 | 5.0 |

TABLE 4-continued

Compositions of first and second modules.

| | NT31 | NT32 | NT33 | NT34 | NT35 | NT36 | NT37 | NT38 | NT39 |
|---|---|---|---|---|---|---|---|---|---|
| Raw material 1$^{st}$ module | | | | Content in weight percent of 1$^{st}$ module | | | | | |
| Mannitol | 85.4 | 85.4 | 85.4 | 85.4 | 85.4 | 85.4 | 85.4 | 85.4 | 85.4 |
| Super-disintegrant | 5 | 5 | 5 | 5 | 5 | 5 | 5 | 5 | 5 |
| Sodium carbonate | 5 | 5 | 5 | 5 | 5 | 5 | 5 | 5 | 5 |
| NBT | 4.1 | 4.1 | 4.1 | 4.1 | 4.1 | 4.1 | 4.1 | 4.1 | 4.1 |
| MgSt | 0.5 | 0.5 | 0.5 | 0.5 | 0.5 | 0.5 | 0.5 | 0.5 | 0.5 |
| Total 1$^{st}$ module | 100 | 100 | 100 | 100 | 100 | 100 | 100 | 100 | 100 |
| Raw material 2$^{nd}$ module | | | | Content in weight percent of 2$^{nd}$ module | | | | | |
| Mannitol | 96.85 | 97.51 | 97.39 | 97.60 | 96.39 | 97.92 | 97.88 | 97.15 | 96.41 |
| Disodium hydrogen citrate | 1.4 | — | — | — | — | — | — | — | — |
| Malic acid | — | 0.74 | — | — | — | — | 0.37 | 1.10 | 1.84 |
| Mono-sodium malate | — | — | 0.86 | — | — | — | — | — | — |
| Succinic acid | — | — | — | 0.65 | — | — | — | — | — |
| Tartaric acid | — | — | — | — | 1.86 | — | — | — | — |
| Acetic acid | — | — | — | — | — | 0.33 | — | — | — |
| Flavor | 1 | 1 | 1 | 1 | 1 | 1 | 1 | 1 | 1 |
| HIS | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 |
| Total 2$^{nd}$ module | 100 | 100 | 100 | 100 | 100 | 100 | 100 | 100 | 100 |

NBT = Nicotine bi-tartrate (nicotine content of 32.38% by weight).
HIS = high intensity sweetener.
*The amount of acidic pH regulating agent in the second module is presented as equivalents relative to the nicotine in the first module.

Alternative ingredients as described in relation to NT1-NT30 may also be applied for NT31-NT39.

Example 2E 300 mg nicotine tablets were made each with 225 mg second module and 75 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 5

Compositions of first and second compressed modules.

| | NT41 | NT42 | NT43 | NT44 | NT45 | NT46 | NT47 | NT48 | NT49 | C3 |
|---|---|---|---|---|---|---|---|---|---|---|
| Nicotine tdose (mg) | 1.0 | 1.0 | 1.0 | 1.0 | 1.0 | 1.0 | 1.0 | 1.0 | 1.0 | 1.0 |
| Acidic pH regulating agent [eq]* | 2.0 | 2.0 | 2.0 | 2.0 | 2.0 | 2.0 | 2.0 | 2.0 | 2.0 | 2.0 |
| Raw material 1$^{st}$ module | | | | Content in weight percent of 1$^{st}$ module | | | | | | |
| Mannitol | 86.4 | 84.4 | 86.4 | 84.4 | 85.4 | 85.4 | 85.4 | 85.4 | 85.4 | 90.4 |
| Super-disintegrant | 5 | 5 | 5 | 5 | 5 | 5 | 5 | 5 | 5 | 5 |
| Sodium carbonate | 3 | 4.5 | 3 | 4.5 | — | — | — | — | — | — |
| Sodium bicarbonate | 1 | 1.5 | 1 | 1.5 | — | — | — | — | — | — |
| Trometamol | — | — | — | — | 5 | 5 | — | — | — | — |
| Disodium hydrogen phosphate | — | — | — | — | — | — | 5 | — | — | — |

TABLE 5-continued

Compositions of first and second compressed modules.

|  | NT41 | NT42 | NT43 | NT44 | NT45 | NT46 | NT47 | NT48 | NT49 | C3 |
|---|---|---|---|---|---|---|---|---|---|---|
| Potassium carbonate | — | — | — | — | — | — | — | 5 | 5 | — |
| NBT | 4.1 | 4.1 | 4.1 | 4.1 | 4.1 | 4.1 | 4.1 | 4.1 | 4.1 | 4.1 |
| MgSt | 0.5 | 0.5 | 0.5 | 0.5 | 0.5 | 0.5 | 0.5 | 0.5 | 0.5 | 0.5 |
| Total 1$^{st}$ module | 100 | 100 | 100 | 100 | 100 | 100 | 100 | 100 | 100 | 100 |
| Raw material 2$^{nd}$ module | Content in weight percent of 2$^{nd}$ module | | | | | | | | | |
| Mannitol | 97.20 | 97.20 | 97.51 | 97.51 | 97.20 | 97.51 | 97.20 | 97.20 | 97.51 | 97.20 |
| Citric acid | 1.05 | 1.05 | — | — | 1.05 | — | 1.05 | 1.05 | — | 1.05 |
| Malic acid | — | — | 0.74 | 0.74 | — | 0.74 | — | — | 0.74 | — |
| Fruit flavor | 1 | 1 | 1 | 1 | 1 | 1 | 1 | 1 | 1 | 1 |
| HIS | 0.25 | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 | 0.5 |
| Total 2$^{nd}$ module | 100 | 100 | 100 | 100 | 100 | 100 | 100 | 100 | 100 | 100 |

NBT = Nicotine bi-tartrate (nicotine content of 32.38% by weight).
HIS = high intensity sweetener.
*The amount of acidic pH regulating agent in the second module is presented as equivalents relative to the nicotine in the first module.

Fruit flavors have been used in NT41-49 and C3.

C3 is a comparative example not comprising alkaline pH regulating agent in the first compressed module.

Alternative ingredients as described in relation to NT1-NT39 may also be applied for NT41-NT49.

Example 2F 300 mg nicotine tablets were made each with 225 mg second module and 75 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 6

Compositions of first and second modules.

|  | NT51 | NT52 | NT53 | NT54 | NT55 | NT56 | NT57 | NT58 | NT59 |
|---|---|---|---|---|---|---|---|---|---|
| Nicotine dose (mg) | 1.0 | 1.0 | 1.0 | 1.0 | 1.0 | 1.0 | 1.0 | 1.0 | 1.0 |
| Acidic pH regulating agent [eq]* | 2.0 | 2.0 | 2.0 | 2.0 | 2.0 | 2.0 | 2.0 | 2.0 | 2.0 |
| Raw material 1$^{st}$ module | Content in weight percent of 1$^{st}$ module | | | | | | | | |
| Mannitol | 86.15 | 76.15 | 66.15 | 56.15 | 46.15 | 36.15 | — | 56.15 | 85.15 |
| Xylitol | — | — | — | — | — | — | — | 30.00 | — |
| Erythritol | — | 10.00 | 20.00 | 30.00 | 40.00 | 50.00 | 86.15 | — | — |
| Super-disintegrant | 5 | 5 | 5 | 5 | 5 | 5 | 5 | 5 | 5 |
| Sodium carbonate | 3 | 4 | 4 | 4 | 4 | 4 | 4 | 4 | 3 |
| Sodium bicarbonate | 1 | — | — | — | — | — | — | — | 1 |
| HIS | 0.25 | 0.25 | 0.25 | 0.25 | 0.25 | 0.25 | 0.25 | 0.25 | 0.25 |
| Flavor | — | — | — | — | — | — | — | — | 1.0 |
| NBT | 4.1 | 4.1 | 4.1 | 4.1 | 4.1 | 4.1 | 4.1 | 4.1 | 4.1 |
| MgSt | 0.5 | 0.5 | 0.5 | 0.5 | 0.5 | 0.5 | 0.5 | 0.5 | 0.5 |
| Total 1$^{st}$ module | 100 | 100 | 100 | 100 | 100 | 100 | 100 | 100 | |
| Raw material 2$^{nd}$ module | Content in weight percent of 2$^{nd}$ module | | | | | | | | |
| Mannitol | 97.20 | — | — | — | — | 50.00 | 50.00 | 50.00 | — |
| Isomalt | — | 97.20 | — | — | — | 47.20 | — | — | 50.00 |
| Sorbitol | — | — | 97.20 | — | — | — | 47.20 | — | 47.20 |
| Xylitol | — | — | — | 97.20 | — | — | — | 47.20 | — |
| Erythritol | — | — | — | — | 97.20 | — | — | — | — |
| Citric acid | 1.05 | 1.05 | 1.05 | 1.05 | 1.05 | 1.05 | 1.05 | 1.05 | 1.05 |
| Flavor | 1 | 1 | 1 | 1 | 1 | 1 | 1 | 1 | 1 |

TABLE 6-continued

Compositions of first and second modules.

| | NT51 | NT52 | NT53 | NT54 | NT55 | NT56 | NT57 | NT58 | NT59 |
|---|---|---|---|---|---|---|---|---|---|
| HIS | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 |
| Total 2$^{nd}$ module | 100 | 100 | 100 | 100 | 100 | 100 | 100 | 100 | 100 |

NBT = Nicotine bi-tartrate (nicotine content of 32.38% by weight).
HIS = high intensity sweetener.
*The amount of acidic pH regulating agent in the second module is presented as equivalents relative to the nicotine in the first module.

Alternative ingredients as described in relation to NT1-NT49 may also be applied for NT51-NT59.

Example 2G 300 mg nicotine tablets were made each with 225 mg second module and 75 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 7

Compositions of first and second compressed modules.

| | NT61 | NT62 | NT63 | NT64 | NT65 | NT66 | NT67 | NT68 | NT69 |
|---|---|---|---|---|---|---|---|---|---|
| Nicotine dose (mg) | 1.0 | 1.0 | 1.0 | 1.0 | 1.0 | 1.0 | 1.0 | 1.0 | 1.0 |
| Acidic pH regulating agent [eq]* | 2.0 | 2.0 | 2.0 | 2.0 | 2.0 | 2.0 | 2.0 | 2.0 | 2.0 |
| Raw material 1$^{st}$ module | \multicolumn{9}{c}{Content in weight percent of 1$^{st}$ module} | | | | | | | | |
| Mannitol | 84.15 | 83.15 | 83.15 | 83.15 | 83.15 | 83.15 | 83.15 | 83.15 | 83.15 |
| crosslinked polyvinyl pyrrolidone | 8.0 | 8.0 | 8.0 | — | — | — | 8.0 | 8.0 | 8.0 |
| crosslinked cellulose | — | — | — | 8.0 | — | — | — | — | — |
| crosslinked starch | — | — | — | — | 8.0 | — | — | — | — |
| crosslinked alginic acid | — | — | — | — | — | 8.0 | — | — | — |
| Sodium carbonate | 3 | 4 | 4 | 4 | 4 | 4 | 4 | 4 | 4 |
| HIS | 0.25 | 0.25 | 0.25 | 0.25 | 0.25 | 0.25 | 0.25 | 0.25 | 0.25 |
| NBT | 4.1 | 4.1 | 4.1 | 4.1 | 4.1 | 4.1 | 4.1 | 4.1 | 4.1 |
| MgSt | 0.5 | 0.5 | 0.5 | 0.5 | 0.5 | 0.5 | 0.5 | 0.5 | 0.5 |
| Total 1$^{st}$ module | 100 | 100 | 100 | 100 | 100 | 100 | 100 | 100 | 100 |
| Raw material 2$^{nd}$ module | | | Content in weight percent of 2$^{nd}$ module | | | | | | |
| Mannitol | 92.20 | 93.20 | 95.20 | 95.20 | 95.20 | 95.20 | 92.20 | 92.20 | 92.20 |
| MCC | 5.0 | 4.0 | 2.0 | 2.0 | 2.0 | 2.0 | — | — | — |
| Sodium alginate | — | — | — | — | — | — | 5.0 | — | — |
| Calcium polycarbophil | — | — | — | — | — | — | — | 5.0 | — |
| Xanthan gum | — | — | — | — | — | — | — | — | 5.0 |
| Citric acid | 1.05 | 1.05 | 1.05 | 1.05 | 1.05 | 1.05 | 1.05 | 1.05 | 1.05 |
| Flavor | 1 | 1 | 1 | 1 | 1 | 1 | 1 | 1 | 1 |
| HIS | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 |
| Total 2$^{nd}$ module | 100 | 100 | 100 | 100 | 100 | 100 | 100 | 100 | 100 |

NBT = Nicotine bi-tartrate (nicotine content of 32.38% by weight).
HIS = high intensity sweetener.
*The amount of acidic pH regulating agent in the second module is presented as equivalents relative to the nicotine in the first module.

Alternative ingredients as described in relation to NT1-NT59 may also be applied for NT61-NT69.

Example 2H 300 mg nicotine tablets were made each with 225 mg second module and 75 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 8

Compositions of first and second modules.

| | NT71 | NT72 | NT73 | NT74 | NT75 | NT76 | NT77 | NT78 | NT79 |
|---|---|---|---|---|---|---|---|---|---|
| Nicotine dose (mg) | 1.0 | 1.0 | 1.0 | 1.0 | 1.0 | 1.0 | 1.0 | 1.0 | 1.0 |
| Acidic pH regulating agent [eq]* | 2.0 | 2.0 | 2.0 | 2.0 | 2.0 | 2.0 | 2.0 | 2.0 | 2.0 |
| Raw material 1$^{st}$ module | Content in weight percent of 1$^{st}$ module | | | | | | | | |
| Mannitol | 81.40 | 83.90 | 86.90 | 81.40 | 83.90 | 86.90 | 81.40 | 83.90 | 86.90 |
| crosslinked polyvinyl pyrrolidone | 10.0 | 7.5 | 5.0 | — | — | — | — | — | — |
| crosslinked cellulose | — | — | — | 10.0 | 7.5 | 5.0 | — | — | — |
| crosslinked starch | — | — | — | — | — | — | 10.0 | 7.5 | 5.0 |
| Sodium carbonate | 4 | 4 | 4 | 4 | 4 | 4 | 4 | 4 | 4 |
| NBT | 4.1 | 4.1 | 4.1 | 4.1 | 4.1 | 4.1 | 4.1 | 4.1 | 4.1 |
| MgSt | 0.5 | 0.5 | — | 0.5 | 0.5 | — | 0.5 | 0.5 | — |
| Total 1$^{st}$ module | 100 | 100 | 100 | 100 | 100 | 100 | 100 | 100 | 100 |
| Raw material 2$^{nd}$ module | Content in weight percent of 2$^{nd}$ module 1 | | | | | | | | |
| Mannitol | 90.95 | 90.95 | 90.95 | 90.95 | 90.95 | 90.95 | 90.95 | 90.95 | 90.95 |
| MCC | 4.0 | 4.0 | 4.0 | 4.0 | 4.0 | 4.0 | 4.0 | 4.0 | 4.0 |
| Citric acid | 1.05 | 1.05 | 1.05 | 1.05 | 1.05 | 1.05 | 1.05 | 1.05 | 1.05 |
| Flavor | 2.7 | 2.7 | 2.7 | 2.7 | 2.7 | 2.7 | 2.7 | 2.7 | 2.7 |
| HIS | 0.3 | 0.3 | 0.3 | 0.3 | 0.3 | 0.3 | 0.3 | 0.3 | 0.3 |
| MgSt | 1.0 | 1.0 | 1.0 | 1.0 | 1.0 | 1.0 | 1.0 | 1.0 | 1.0 |
| Total 2$^{nd}$ module | 100 | 100 | 100 | 100 | 100 | 100 | 100 | 100 | 100 |

NBT = Nicotine bi-tartrate (nicotine content of 32.38% by weight).

HIS = high intensity sweetener.

*The amount of acidic pH regulating agent in the second module is presented as equivalents relative to the nicotine in the first module.

Alternative ingredients as described in relation to NT1-NT69 may also be applied for NT71-NT79.

Example 21—Nicotine Sources and Glidant 500 mg nicotine tablets were made each with 350 mg second module and 150 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 9

Compositions of first and second modules.

|  | NT81 | NT82 | NT83 | NT84 | NT85 | NT86 | NT87 | NT88 | NT89 |
|---|---|---|---|---|---|---|---|---|---|
| Nicotine dose (mg) | 1.0 | 1.0 | 1.0 | 1.0 | 1.0 | 1.0 | 1.0 | 1.0 | 1.0 |
| Acidic pH regulating agent [eq]* | 3.5 | 3.5 | 3.5 | 3.5 | 3.5 | 3.5 | 3.5 | 3.5 | 3.5 |
| Raw material 1st module | Content in weight percent of 1st module | | | | | | | | |
| Mannitol | 88.83 | 87.50 | 87.50 | 87.50 | 87.50 | — | — | 85.90 | 55.90 |
| Erythritol | — | — | — | — | — | 87.50 | 87.50 | — | 30 |
| Super disintegrant | 5.0 | 5.0 | 5.0 | 5.0 | 5.0 | 5.0 | 5.0 | 5.0 | 5.0 |
| Sodium carbonate | 5.0 | 5.0 | 5.0 | 5.0 | 5.0 | 5.0 | 5.0 | 5.0 | 5.0 |
| NBT | — | — | — | — | — | — | — | 2.1 | 2.1 |
| Nicotine free base | 0.67 | — | — | — | — | — | — | — | — |
| Nicotine-calcium carbonate** | — | 2.0 | — | — | — | — | — | — | — |
| Nicotine-MCC** | — | — | 2.0 | — | — | 2.0 | — | — | — |
| Nicotine-soluble fiber** | — | — | — | 2.0 | — | — | — | — | — |
| Nicotine-sugar alcohol** | — | — | — | — | 2.0 | — | 2.0 | — | — |
| MgSt | 0.5 | 0.5 | 0.5 | 0.5 | 0.5 | 0.5 | 0.5 | — | — |
| Sodium stearyl fumerate | — | — | — | — | — | — | — | 2.0 | 2.0 |
| Total 1st module | 100 | 100 | 100 | 100 | 100 | 100 | 100 | 100 | 100 |
| Raw material 2nd module | Content in weight percent of 2nd module | | | | | | | | |
| Mannitol | 90.80 | 90.80 | 90.80 | 90.80 | 90.80 | 90.80 | 90.80 | 40.80 | 90.80 |
| Isomalt | — | — | — | — | — | — | — | 50.00 | — |
| MCC | 3.0 | 3.0 | 3.0 | 3.0 | 3.0 | 3.0 | 3.0 | 3.0 | 3.0 |
| Citric acid | 1.2 | 1.2 | 1.2 | 1.2 | 1.2 | 1.2 | 1.2 | 1.2 | 1.2 |
| Flavor | 3.6 | 3.6 | 3.6 | 3.6 | 3.6 | 3.6 | 3.6 | 3.6 | 3.6 |
| HIS | 0.4 | 0.4 | 0.4 | 0.4 | 0.4 | 0.4 | 0.4 | 0.4 | 0.4 |
| MgSt | 1.0 | 1.0 | 1.0 | 1.0 | 1.0 | 1.0 | 1.0 | 1.0 | 1.0 |
| Total 2nd module | 100 | 100 | 100 | 100 | 100 | 100 | 100 | 100 | 100 |

NBT = Nicotine bi-tartrate (nicotine content of 32.38% by weight).
HIS = high intensity sweetener.
*The amount of acidic pH regulating agent in the second module is presented as equivalents relative to the nicotine in the first module.
**free nicotine base sorbed onto carrier in a weight ratio of 1:2

Alternative ingredients as described in relation to NT1-NT79 may also be applied for NT81-NT89.

Example 2J 500 mg nicotine tablets were made each with 350 mg second module and 150 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 10A

Compositions of first and second compressed modules.

| | NT91 | NT92 | NT93 | NT94 | NT95 | NT96 | NT97 | NT98 | C4 |
|---|---|---|---|---|---|---|---|---|---|
| Nicotine dose (mg) | 1.0 | 1.0 | 1.0 | 1.0 | 1.0 | 1.0 | 1.0 | 1.0 | 1.0 |
| Acidic pH regulating agent [eq]* | 3.5 | 3.5 | 3.5 | 3.5 | 3.5 | 3.5 | 3.5 | 3.5 | 3.5 |
| Raw material $1^{st}$ module | \multicolumn{9}{c}{Content in weight percent of $1^{st}$ module} |
| Mannitol | 87.15 | 87.15 | 87.15 | 87.15 | 87.15 | 87.15 | 87.15 | 87.15 | 87.15 |
| Super disintegrant | 5.0 | 5.0 | 5.0 | 5.0 | 5.0 | 5.0 | 5.0 | 5.0 | 5.0 |
| Sodium carbonate | 5.0 | 5.0 | 5.0 | 5.0 | 5.0 | 5.0 | 5.0 | 5.0 | 5.0 |
| HIS | 0.25 | 0.25 | 0.25 | 0.25 | 0.25 | 0.25 | 0.25 | 0.25 | 0.25 |
| NBT | 2.1 | 2.1 | 2.1 | 2.1 | 2.1 | 2.1 | 2.1 | 2.1 | 2.1 |
| MgSt | 0.5 | 0.5 | 0.5 | 0.5 | 0.5 | 0.5 | 0.5 | 0.5 | 0.5 |
| Total $1^{st}$ module | 100 | 100 | 100 | 100 | 100 | 100 | 100 | 100 | 100 |
| Raw material $2^{nd}$ module | \multicolumn{9}{c}{Content in weight percent of $2^{nd}$ module} |
| Mannitol | 95.55 | 95.92 | 95.05 | 95.42 | 94.05 | 94.42 | 93.05 | 93.42 | 94.25 |
| MCC | 2.0 | 2.0 | 2.0 | 2.0 | 2.0 | 2.0 | 2.0 | 2.0 | 2.0 |
| Citric acid | 1.2 | — | 1.2 | — | 1.2 | — | 1.2 | — | — |
| Malic acid | — | 0.83 | — | 0.83 | — | 0.83 | — | 0.83 | — |
| Fruit flavor | 0.5 | 0.5 | 1.0 | 1.0 | 2.0 | 2.0 | 3.0 | 3.0 | 3.0 |
| HIS | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 |
| Total $2^{nd}$ module | 100 | 100 | 100 | 100 | 100 | 100 | 100 | 100 | 100 |

NBT = Nicotine bi-tartrate (nicotine content of 32.38% by weight).

HIS = high intensity sweetener.

*The amount of acidic pH regulating agent in the second module is presented as equivalents relative to the nicotine in the first module.

Alternative ingredients as described in relation to NT1-NT89 may also be applied for NT91-NT98.

Example 2K 300 mg nicotine tablets were made each with 200 mg second module and 100 mg first module. The tablets were prepared according to example 1C, i.e. a layered design. However, the tablets could alternatively have been prepared according to example 1A or 1B.

Punch used: 10.00 mm, circular, shallow concave, D tooling.

The second compressed module is compressed at a compression force of about 3 kN, after which the first module is fused by compression to the second module at a compression force of about 15-20 kN.

TABLE 10B

Compositions of first and second compressed modules.

|  | NT101 | NT102 | NT103 | NT104 | NT105 | NT106 | NT107 | NT108 | C5 |
|---|---|---|---|---|---|---|---|---|---|
| Nicotine dose (mg) | 1.0 | 1.0 | 1.0 | 1.0 | 1.0 | 1.0 | 1.0 | 1.0 | 1.0 |
| Acidic pH regulating agent [eq]* | 5.1 | 3.4 | 0.85 | 5.1 | 3.6 | 3.4 | 3.4 | 3.4 | — |
| Raw material 1st module | Content in weight percent of 1st module | | | | | | | | |
| Mannitol | 80.4 | 80.4 | 80.4 | 80.4 | 80.4 | 80.4 | 80.4 | 80.4 | 80.4 |
| Super disintegrant | 8.0 | 8.0 | 8.0 | 8.0 | 8.0 | 8.0 | 8.0 | 8.0 | 8.0 |
| Sodium carbonate | 5.0 | 5.0 | 5.0 | 5.0 | 5.0 | 5.0 | 5.0 | 5.0 | 5.0 |
| MCC | 3.0 | 3.0 | 3.0 | 3.0 | 3.0 | 3.0 | 3.0 | 3.0 | 3.0 |
| NBT | 3.1 | 3.1 | 3.1 | 3.1 | 3.1 | 3.1 | 3.1 | 3.1 | 3.1 |
| MgSt | 0.5 | 0.5 | 0.5 | 0.5 | 0.5 | 0.5 | 0.5 | 0.5 | 0.5 |
| Total 1st module | 100 | 100 | 100 | 100 | 100 | 100 | 100 | 100 | 100 |
| Raw material 2nd module | Content in weight percent of 2nd module | | | | | | | | |
| Mannitol | 89.9 | 90.9 | 92.4 | 88.9 | 90.23 | 90.9 | 90.9 | 90.9 | 92.9 |
| Blue color | 0.1 | 0.1 | 0.1 | 0.1 | 0.1 | 0.1 | 0.1 | 0.1 | 0.1 |
| MCC | 2.5 | 2.5 | 2.5 | 2.5 | 2.5 | 2.5 | 2.5 | 2.5 | 2.5 |
| Citric acid | 3.0 | 2.0 | 0.5 | — | — | 2.0 | 2.0 | 2.0 | — |
| $NaH_2PO_4$ | — | — | — | 2.67 | 2.67 | — | — | — | — |
| $Na_2HPO_4$ | — | — | — | 1.33 | — | — | — | — | — |
| Fruit flavor | 2.0 | 2.0 | 2.0 | 2.0 | 2.0 | 2.0 | 2.0 | 2.0 | 2.0 |
| HIS | 1.5 | 1.5 | 1.5 | 1.5 | 1.5 | 1.5 | 1.5 | 1.5 | 1.5 |
| MgSt | 1.0 | 1.0 | 1.0 | 1.0 | 1.0 | 1.0 | 1.0 | 1.0 | 1.0 |
| Total 2nd module | 100 | 100 | 100 | 100 | 100 | 100 | 100 | 100 | 100 |

NBT = Nicotine bi-tartrate (nicotine content of 32.38% by weight).

$NaH_2PO_4$ = Mono sodium dihydrogen phosphate.

$Na_2HPO_4$ = Di-sodium hydrogen phosphate.

HIS = high intensity sweetener.

*The amount of acidic pH regulating agent in the second module is presented as equivalents relative to the nicotine in the first module. Where the acidic pH regulating agent is mixture of pH regulating agents, the molar ratio refers to the total molar amount of acidic pH regulating agent(s) relative to the molar amount of nicotine in the first compressed module.

Alternative ingredients as described in relation to NT1-NT98 may also be applied for NT101-10 NT108.

For the samples 106, 107 and 108 the compression force was adjusted to provide nicotine tablets with different hardness (breaking force):

TABLE 10C

Nicotine tablets with different hardness (breaking force).

| Sample | Hardness, N |
|---|---|
| 106 | 65 |
| 107 | 85 |
| 108 | 105 |

Example 3A: In Vivo Disintegration Time of First Compressed Module

The in vivo disintegration time of the first compressed module may be determined using a coloring agent. Nicotine tablets were prepared by adding a coloring agent to the second compressed module, whereby at two-colored tablet is obtained.

A sample tablet comprising a colored second compressed module was tested in a test panel of 8 test persons. Test subjects abstain from eating and drinking at least 30 minutes before initiation of any test. The test person was a healthy person appointed on an objective basis according to specified requirements.

For testing the tablet was placed in the mouth, between the tongue and the palate.

The tablet was visually inspected for every 5 seconds, to determine the time where the un-colored, white first compressed module has fully disintegrated, i.e. the time where no white color is observed at the residual tablet.

TABLE 11 in vivo disintegration of first compressed module.

| | NT102 | NT103 | NT104 | C5 |
|---|---|---|---|---|
| | \multicolumn{4}{c}{Acidic pH regulating agent [eq.]} | |
| | Citric acid [3.4 eq.] | Citric acid [0.85 eq.] | Monosodium dihydrogen phosphate - disodium hydrogen phosphate mixture [5.1 eq.] | None |
| Time points | White r | White | White | White |
| 0 | + | + | + | + |
| 5 sec. | + | + | + | + |

TABLE 11-continued in vivo disintegration of first compressed module.

| | NT102 | NT103 | NT104 | C5 |
|---|---|---|---|---|
| | | Acidic pH regulating agent [eq.] | | |
| | Citric acid [3.4 eq.] | Citric acid [0.85 eq.] | Monosodium dihydrogen phosphate - disodium hydrogen phosphate mixture [5.1 eq.] | None |
| Time points | White r | White | White | White |
| 10 sec. | + | + | + | + |
| 15 sec. | − | − | − | − |
| 20 sec. | − | − | − | − |

Conclusion: the first disintegrating modules were found to have desirable low disintegration time of below 15 seconds.

Example 3B: In Vivo Disintegration Time of Nicotine Tablet

A sample tablet was tested in a test panel of 8 test persons. Test subjects abstain from eating and drinking at least 30 minutes before initiation of any test. The test person was a healthy person appointed on an objective basis according to specified requirements.

The test persons were instructed to swallow saliva after 1 minute and not before that time point. The test persons report the time, where they sense full disintegration of the tablet. The average disintegration time reported by the test persons is calculated for each tablet.

TABLE 12A in vivo disintegration time of nicotine tablets.

| | NT102 | NT103 | NT104 | C5 |
|---|---|---|---|---|
| | | Acidic pH regulating agent [eq.] | | |
| | Citric acid [3.4 eq.] | Citric acid [0.85 eq.] | Monosodium dihydrogen phosphate-disodium hydrogen phosphate mixture [5.1 eq.] | None |
| Average disintegration time | 4 min. 0 sec. | 4 min. 25 sec. | 4 min. 5 sec. | 4 min. 10 sec. |

Conclusion: the tested tablets were all found to have a disintegration time of below 5 min.

In vivo disintegration time was also tested for nicotine tablets of samples 106, 107 and 108 with different hardness (breaking force):

TABLE 12B

In vivo disintegration time of Nicotine tablets with different hardness (breaking force).

| Sample | Hardness, N | Average disintegration time, [m:ss] |
|---|---|---|
| 106 | 65 | 3:00 |
| 107 | 85 | 4:00 |
| 108 | 105 | 4:50 |

Example 3C: In Vivo Testing of Release of Ph Regulating Agents

A sample tablet was tested in a test panel of 8 test persons. Test subjects abstain from eating and drinking at least 30 minutes before initiation of any test. The test person was a healthy person appointed on an objective basis according to specified requirements.

For testing the tablet was placed in the mouth, between the tongue and the palate. The test persons were instructed to swallow saliva after pH measurement performed at 1 minute, and not before that time point.

After 0, 0.5, 1, 2, 3 and 5 minutes, the saliva pH was measured at desired time points (15, 30, 45 second, 1, 1.5, 2, 3, 4 and 5 minutes). The saliva pH was measured directly in the oral saliva using standard pH strips.

The average saliva pH of the test persons is calculated at the different time.

Applying the method outlined above, an in vivo pH profile was obtained for selected samples.

| Time points | NT102 Citric acid [3.4 eq.] Saliva pH | NT103 Citric acid [0.85 eq.] Saliva pH | NT104 Monosodium dihydrogen phosphate-disodium hydrogen phosphate mixture [5.1 eq.] Saliva pH | C5 None Saliva pH |
|---|---|---|---|---|
| | Acidic pH regulating agent [eq.] | | | |
| 0 | 6.8 | 6.8 | 6.8 | 6.8 |
| 15 sec. | 10 | 10 | 10 | 9.5 |
| 30 sec. | 9.0 | 9.5 | 9.5 | 9.0 |
| 45 sec. | 8.7 | 8.1 | 8.7 | 8.7 |
| 1 min. | 8.3 | 8.1 | 8.3 | 8.3 |
| 1 min. 30 sec. | 7.3 | <6.5 | 7.4 | 7.9 |
| 2 min. | 6.8 | <6.5 | 7.4 | 7.7 |
| 3 min. | 6.8 | <6.5 | 7.1 | 7.7 |
| 4 min. | 6.8 | <6.5 | 7.1 | 7.7 |
| 5 min. | 6.8 | 6.8 | 7.4 | 7.1 |

Conclusion: The test demonstrates that tablets comprising an alkaling pH regulating agent in the first compressed module and comprising an acidic pH regulating agent in the second compressed module provide a desirable pH profile, i.e. a desirable pH above 7.5 during the initial time of use followed by a reduction in pH to below 7.5.

Example 3D: Evaluation of Burning Sensation in the Oral Cavity and Throat

Nicotine burning was evaluated by a test panel of 10 trained assessors. At first calibration of nicotine burning was made by means of placing a representative standard nicotine tablet in the mouth, between the tongue and the palate and sucking it to complete disintegration. For this purpose tablets corresponding to the first module of sample C5 were used. Then, each assessor evaluates the burning sensation in the oral cavity and in the throat on a scale from 1 to 15, where 15 is the most intense burning. Each assessor evaluates all samples twice. The evaluations are noted for the time periods indicated. Average values are calculated.

| | NT102 | | C5 | |
|---|---|---|---|---|
| | Acidic pH regulating agent [eq.] | | | |
| | 3.4 | | none | |
| | Burning score (1-15) | | | |
| Time points | Oral | Throat | Oral | Throat |
| 1 min. | 5.7 | 3.8 | 6.5 | 3.8 |
| 2 min. | 4.5 | 3.8 | 5.7 | 5.2 |
| 3 min. | 2.4 | 3.5 | 3.6 | 4.9 |
| 4 min. | 1.2 | 2.4 | 2.0 | 3.7 |
| 5 min. | 0.4 | 2.5 | 1.0 | 3.6 |
| 6 min. | 0.4 | 2.1 | 0.7 | 3.3 |
| 8 min. | 0.1 | 1.6 | 0.2 | 2.2 |
| 10 min. | 0.1 | 1.2 | 0.1 | 1.5 |

Conclusion: The test demonstrates that the tablet comprising an acidic pH regulating agent in the second compressed module is given a significant lower burning score at all time points compared to a comparative tablet not comprising acidic pH regulating agent. The tablets comprising an acidic pH regulating agent in the second compressed module were given a lower burning score both in relation to burning sensation in the oral cavity and in the throat.

The invention claimed is:

1. A water-dissolvable nicotine tablet comprising at least a first compressed module and a second compressed module,
   wherein the first compressed module is a fast disintegrating tablet-module and comprises
      nicotine,
      alkaline pH regulating agent, and
      disintegrant;
   wherein the second compressed module is a lozenge-module and comprises
      acidic pH regulating agent;
   wherein the first compressed module is fully disintegrated within 60 seconds upon oral administration;
   wherein the first compressed module comprises disintegrant in an amount of at least 0.5% by weight of the first compressed module;
   wherein the disintegrant comprises a super disintegrant selected from the group consisting of crosslinked cellulose, crosslinked polyvinyl pyrrolidone, crosslinked starch, crosslinked alginic acid, and any combinations thereof; and
   wherein the first compressed module constitutes between 10% to 50% by weight of the nicotine tablet.

2. The water-dissolvable nicotine tablet according to claim 1, wherein the water-dissolvable nicotine tablet comprises nicotine in an amount of at least 0.2 mg.

3. The water-dissolvable nicotine tablet according to claim 1, wherein the nicotine is comprised in the first compressed module.

4. The water-dissolvable nicotine tablet according to claim 1, wherein the nicotine is selected from the group consisting of nicotine free base, nicotine salts, and combinations thereof.

5. The water-dissolvable nicotine tablet according to claim 1, wherein the first compressed module comprises alkaline pH regulating agent in an amount of at least 0.2% by weight of the first compressed module.

6. The water-dissolvable nicotine tablet according to claim 1, wherein the alkaline pH regulating agent comprises alkaline pH regulating agent selected from the group consisting of sodium carbonate, sodium bicarbonate, potassium carbonate, potassium bicarbonate, trometamol, amino acids, di-alkali hydrogen phosphate, tri-alkali phosphate, and any combination thereof.

7. The water-dissolvable nicotine tablet according to claim 1, wherein the first compressed module induces a pH higher than 7.5 upon dissolution in water having a pH of 7.0, when measured at 25 degrees Celsius and atmospheric pressure.

8. The water-dissolvable nicotine tablet according to claim 1, wherein the second compressed module comprises acidic pH regulating agent in a molar ratio of at most 10 relative to the nicotine in the first compressed module.

9. The water-dissolvable nicotine tablet according to claim 1, wherein the acidic pH regulating agent comprises acidic pH regulating agent selected from the group consisting of phosphoric acid, mono-alkali dihydrogen phosphate, citric acid, mono-alkali dihydrogen citrate, di-alkali hydrogen citrate, malic acid, mono-alkali malate, succinic acid, mono-alkali succinate, tartaric acid, mono-alkali tartrate, acetic acid, sorbic acid, benzoic acid, formic acid, and combinations thereof.

10. The water-dissolvable nicotine tablet according to claim 1, wherein the second compressed module induces a pH lower than 7.5 upon dissolution in water having a pH of 7.0, when measured at 25 degrees Celsius and atmospheric pressure.

11. The water-dissolvable nicotine tablet according to claim 1, wherein the nicotine tablet comprises flavor.

12. The water-dissolvable nicotine tablet according to claim 11, wherein the flavor is comprised in the second compressed module.

13. The water-dissolvable nicotine tablet according to claim 1, wherein the nicotine tablet comprises sugar alcohol in an amount of at least 50% by weight of the nicotine tablet.

14. The water-dissolvable nicotine tablet according to claim 1, wherein the first and the second compressed modules comprise sugar alcohol.

15. The water-dissolvable nicotine tablet according to claim 14, wherein the sugar alcohol of the first compressed module is selected from the group consisting of xylitol, maltitol, mannitol, erythritol, isomalt, sorbitol, lactitol and any combination thereof.

16. The water-dissolvable nicotine tablet according to claim 14, wherein the sugar alcohol of the second compressed module is selected from the group consisting of xylitol, maltitol, mannitol, erythritol, isomalt, sorbitol, lactitol and any combination thereof.

17. The water-dissolvable nicotine tablet according to claim 1, wherein the second compressed module comprises binder in an amount of between 1 and 10% by weight of the second compressed module.

18. The water-dissolvable nicotine tablet according to claim 1, wherein the first compressed module and the second compressed module are tablet layers.

* * * * *